(12) United States Patent
Termanini et al.

(10) Patent No.: US 11,141,279 B2
(45) Date of Patent: Oct. 12, 2021

(54) RECONFIGURABLE HIP PROSTHESIS, METHOD OF USE AND KIT

(71) Applicant: HIP INNOVATION TECHNOLOGY, LLC, Boca Raton, FL (US)

(72) Inventors: Zafer Termanini, Boca Raton, FL (US); George Diamantoni, Boca Raton, FL (US); Brian Vanhiel, Boca Raton, FL (US); Taylor Davis, Boca Raton, FL (US)

(73) Assignee: HIP INNOVATION TECHNOLOGY, LLC, Boca Raton, FL (US)

( * ) Notice: Subject to any disclaimer, the term of this patent is extended or adjusted under 35 U.S.C. 154(b) by 0 days.

(21) Appl. No.: 15/983,576

(22) Filed: May 18, 2018

(65) Prior Publication Data

US 2018/0333265 A1 Nov. 22, 2018

Related U.S. Application Data

(60) Provisional application No. 62/509,304, filed on May 22, 2017.

(51) Int. Cl.
*A61F 2/34* (2006.01)
*A61F 2/36* (2006.01)
(Continued)

(52) U.S. Cl.
CPC .............. *A61F 2/3607* (2013.01); *A61F 2/34* (2013.01); *A61F 2/3609* (2013.01);
(Continued)

(58) Field of Classification Search
CPC ........ A61F 2/34; A61F 2/3607; A61F 2/3609; A61F 2/4081
See application file for complete search history.

(56) References Cited

U.S. PATENT DOCUMENTS

| 5,030,238 A | 7/1991 | Nieder |
| 5,462,563 A | 10/1995 | Shearer et al. |

(Continued)

FOREIGN PATENT DOCUMENTS

| WO | 2017019325 A1 | 2/2017 |
| WO | 2017019328 A1 | 2/2017 |

(Continued)

OTHER PUBLICATIONS

International Search Report for corresponding application PCT/US2018/033388 dated Aug. 7, 2018.

*Primary Examiner* — Brian A Dukert
(74) *Attorney, Agent, or Firm* — Norris McLaughlin PA

(57) ABSTRACT

Disclosed is a reconfigurable hip joint prosthesis and elements therefor which is adapted to be surgically implantable in a human body, a part in the upper femur, another part in the pelvis. The implantable prosthesis may be configured in a reversible manner, and provide alternative configurations as may be desired or necessary. The present invention also includes a method of implanting into a human body a prosthesis as described herein, and subsequently reconfiguring the prosthesis as may be desired or necessary. A still further aspect of the invention is a kit of component parts used in providing a configured implantable prosthesis.

10 Claims, 24 Drawing Sheets

(51) Int. Cl.
*A61F 2/40* (2006.01)
*A61F 2/30* (2006.01)

(52) U.S. Cl.
CPC ....... *A61F 2/30734* (2013.01); *A61F 2/30749* (2013.01); *A61F 2/4081* (2013.01); *A61F 2002/30607* (2013.01); *A61F 2002/30738* (2013.01); *A61F 2002/3483* (2013.01); *A61F 2002/3613* (2013.01); *A61F 2002/3615* (2013.01); *A61F 2002/3652* (2013.01)

(56) References Cited

U.S. PATENT DOCUMENTS

| | | | |
|---|---|---|---|
| 7,470,287 B2* | 12/2008 | Tornier | A61F 2/32 623/19.11 |
| 7,641,698 B1* | 1/2010 | Gibbs | A61F 2/30739 623/22.15 |
| 8,313,531 B2 | 11/2012 | Termanini | |
| 8,323,346 B2 | 12/2012 | Tepic | |
| 8,845,743 B2 | 9/2014 | Termanini | |
| 8,992,627 B2 | 3/2015 | Termanini | |
| 9,005,306 B2 | 4/2015 | Kellar | |
| 9,119,724 B2* | 9/2015 | Termanini | A61F 2/3609 |
| 9,522,067 B2* | 12/2016 | Frankie | A61F 2/4081 |
| 2008/0091274 A1 | 4/2008 | Murphy | |
| 2011/0118846 A1* | 5/2011 | Katrana | A61F 2/4014 623/19.13 |
| 2011/0224798 A1 | 9/2011 | Caillouette | |

FOREIGN PATENT DOCUMENTS

| | | |
|---|---|---|
| WO | 2017019329 A1 | 2/2017 |
| WO | 2017019330 A1 | 2/2017 |
| WO | 2017019332 A1 | 2/2017 |
| WO | 2019019327 A1 | 2/2017 |
| WO | 2017034845 A1 | 3/2017 |
| WO | 2017034846 A1 | 3/2017 |
| WO | 2018026430 A1 | 2/2018 |

* cited by examiner

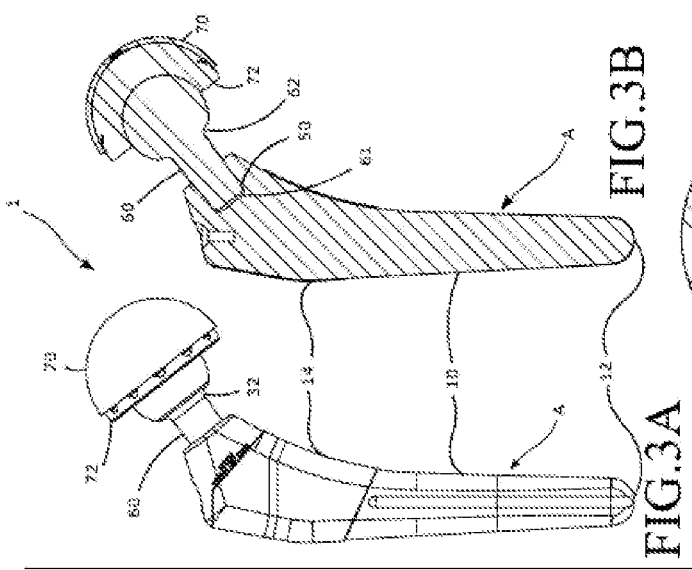
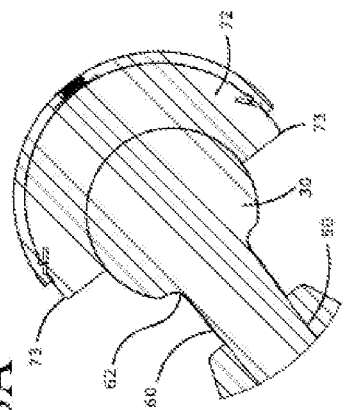
FIG.1A  FIG.1B  FIG.1C
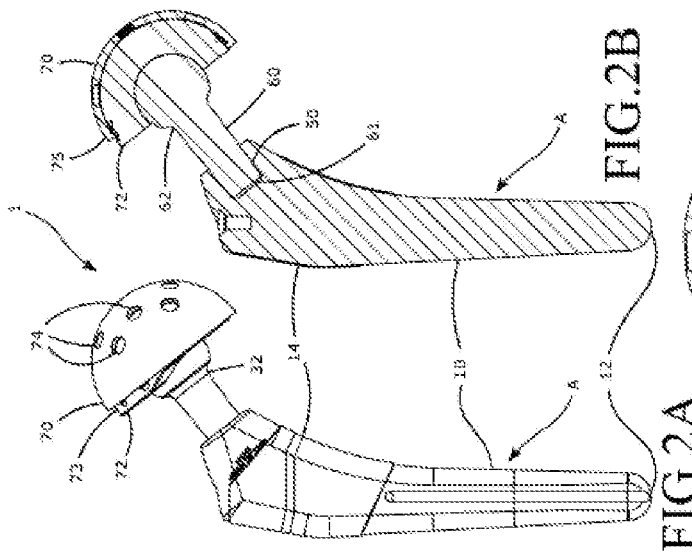
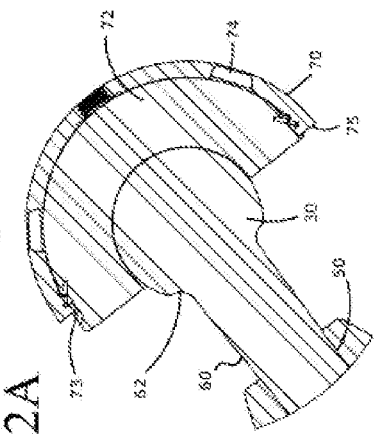
FIG.2A  FIG.2B  FIG.2C
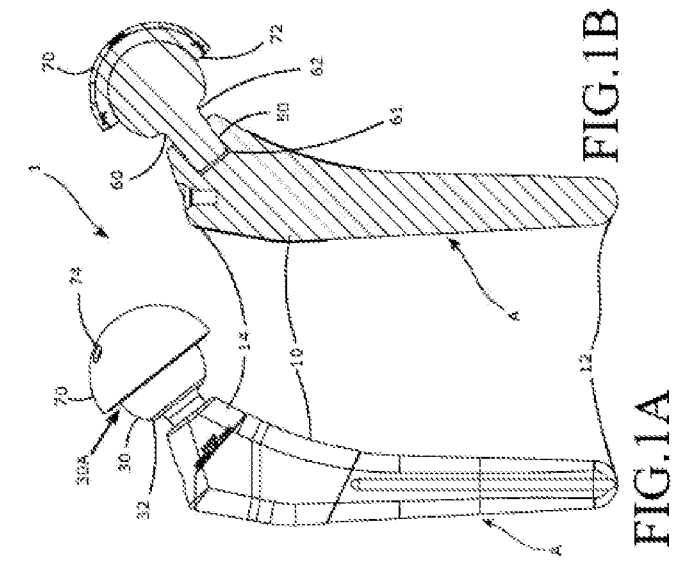
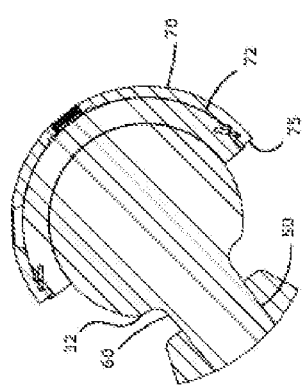
FIG.3A  FIG.3B  FIG.3C

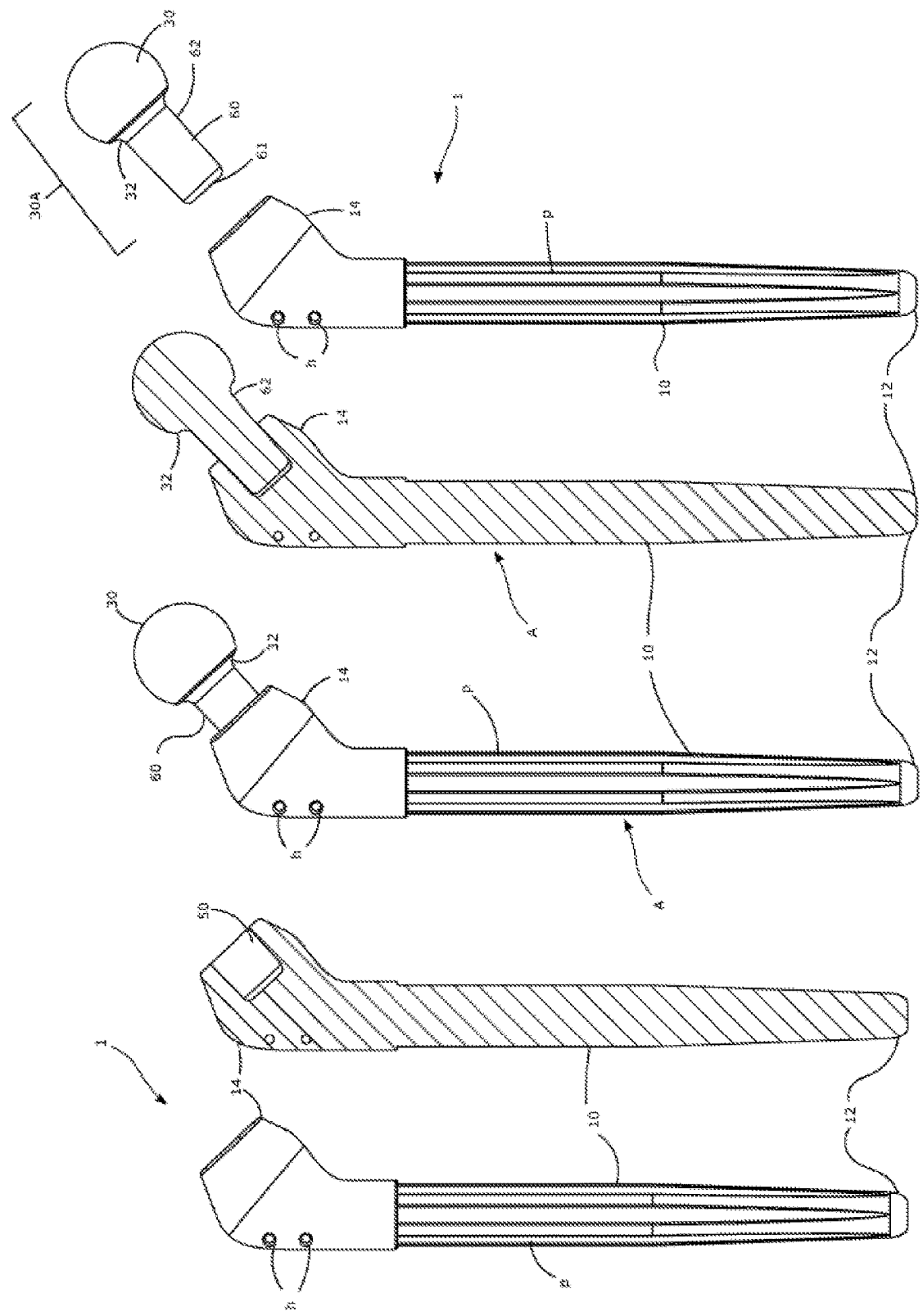

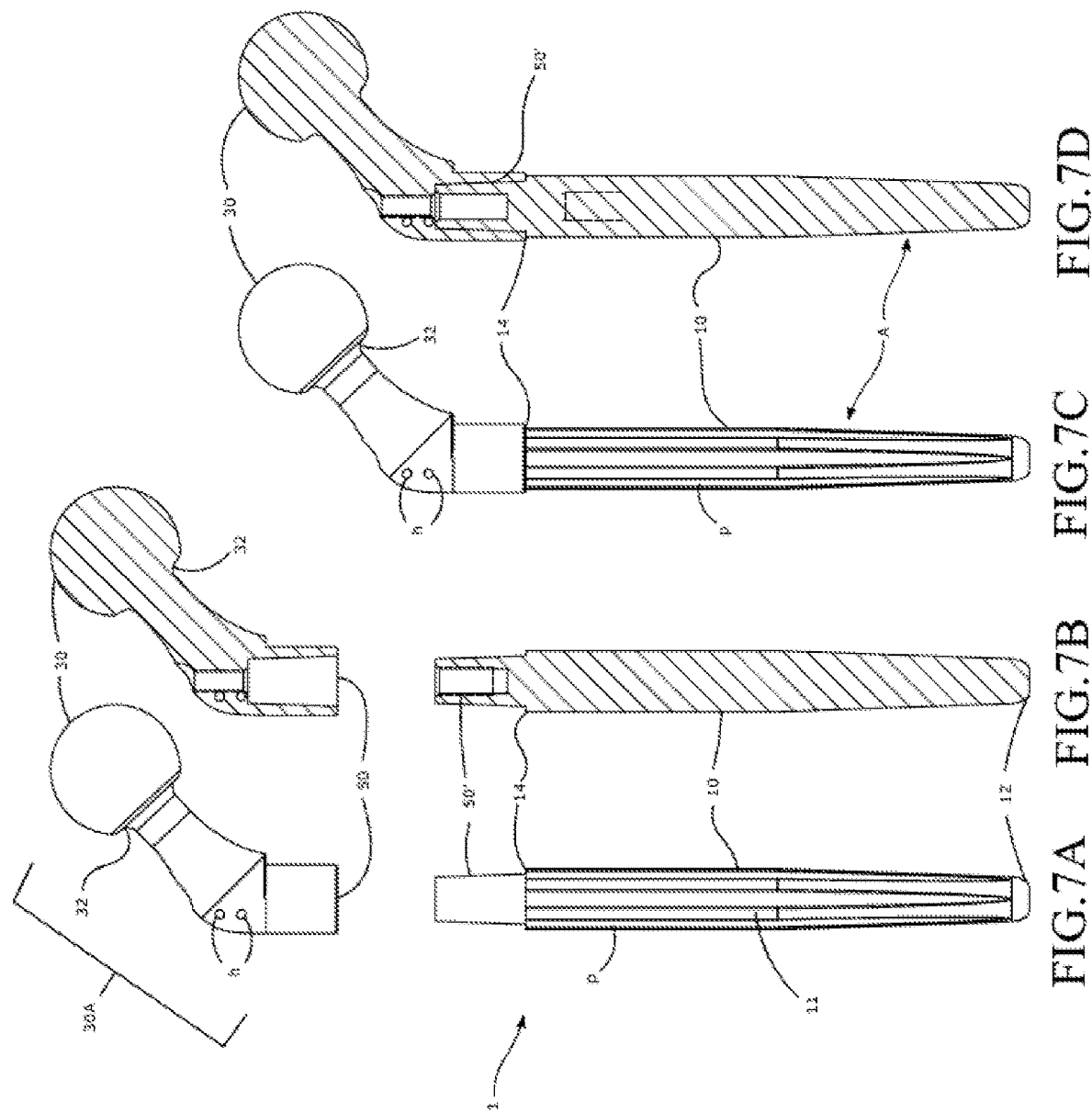

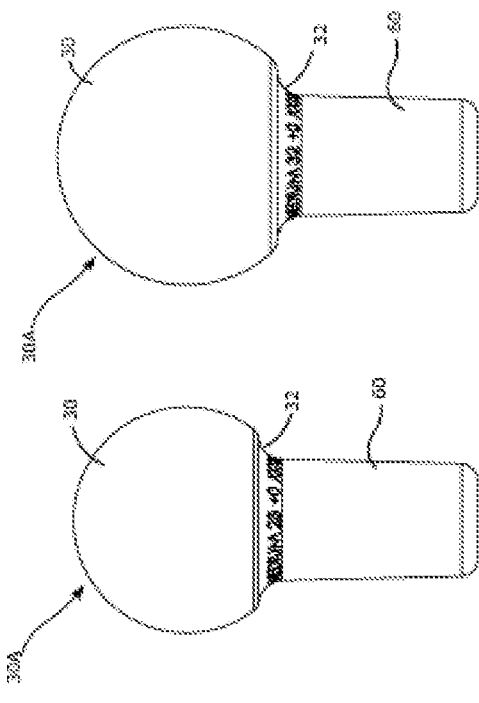
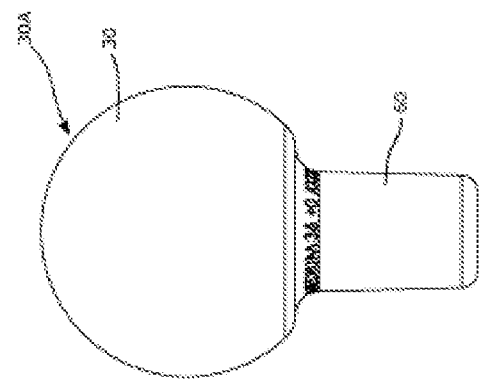
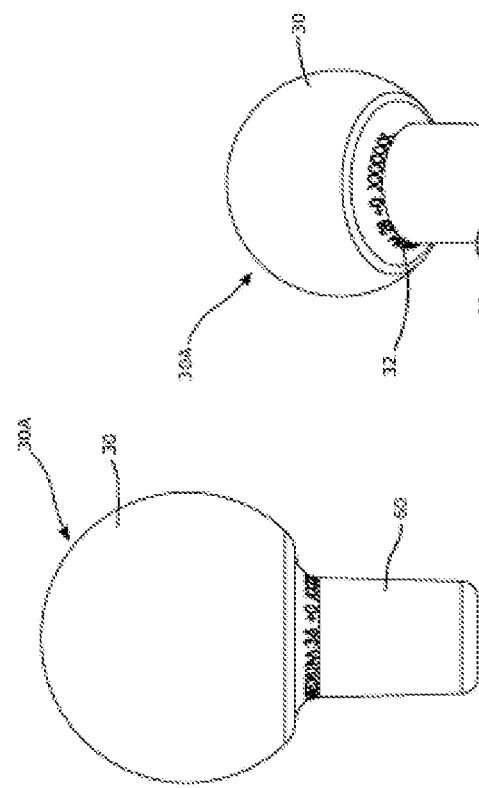
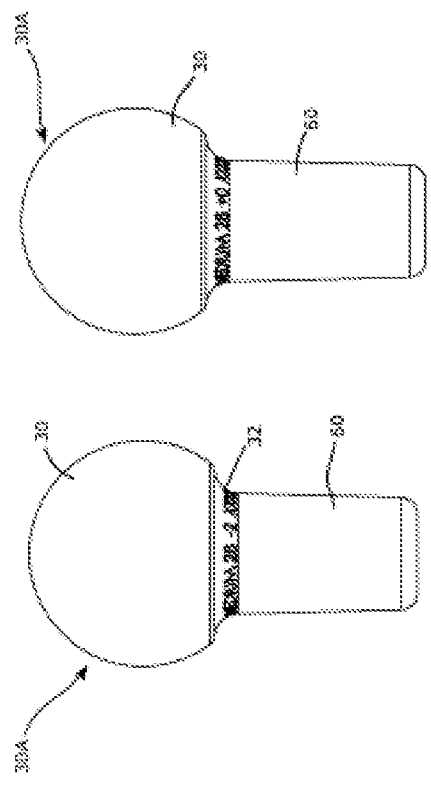
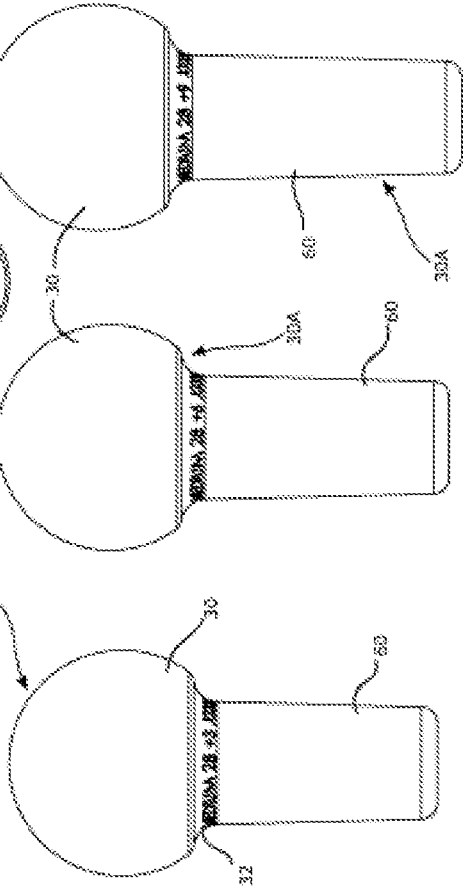
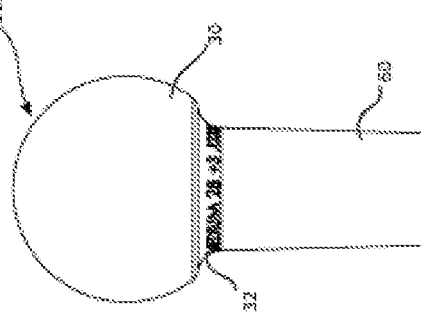
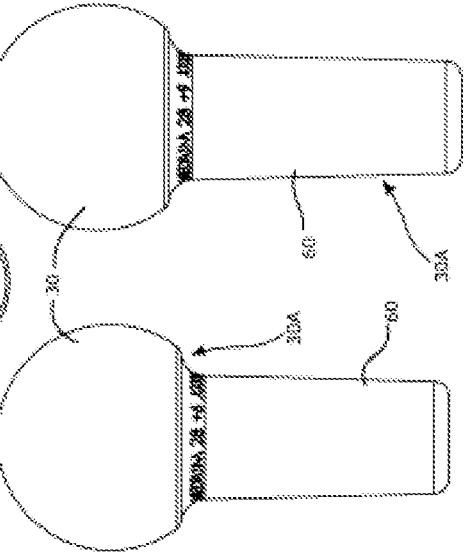
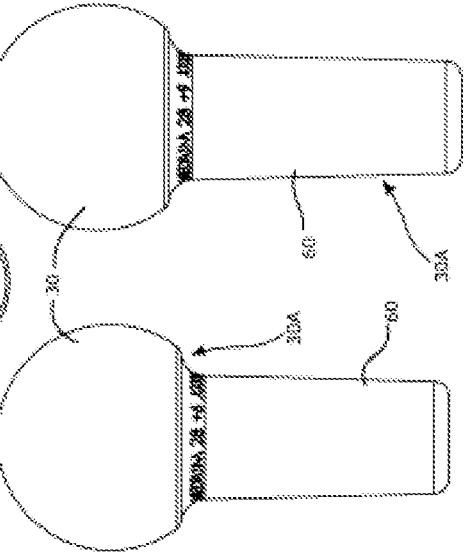
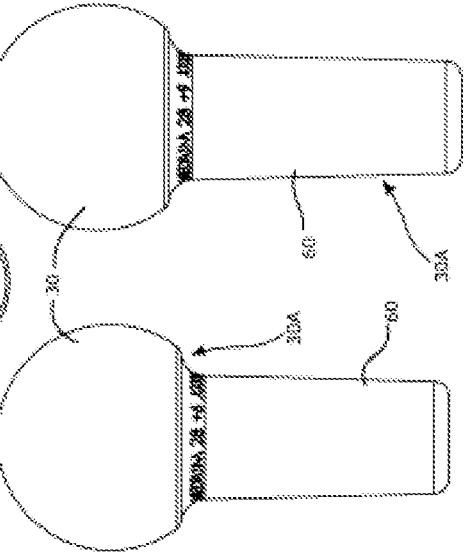

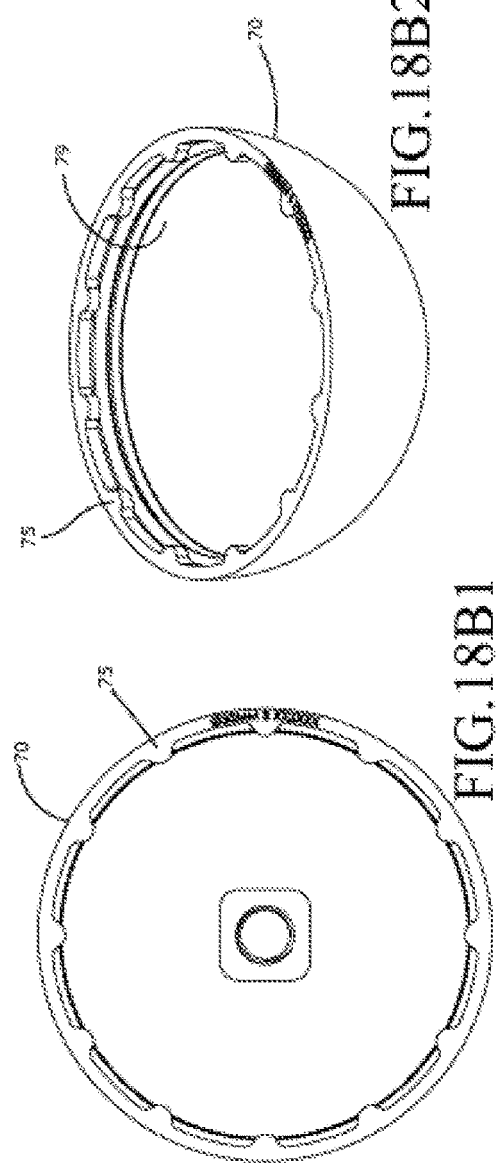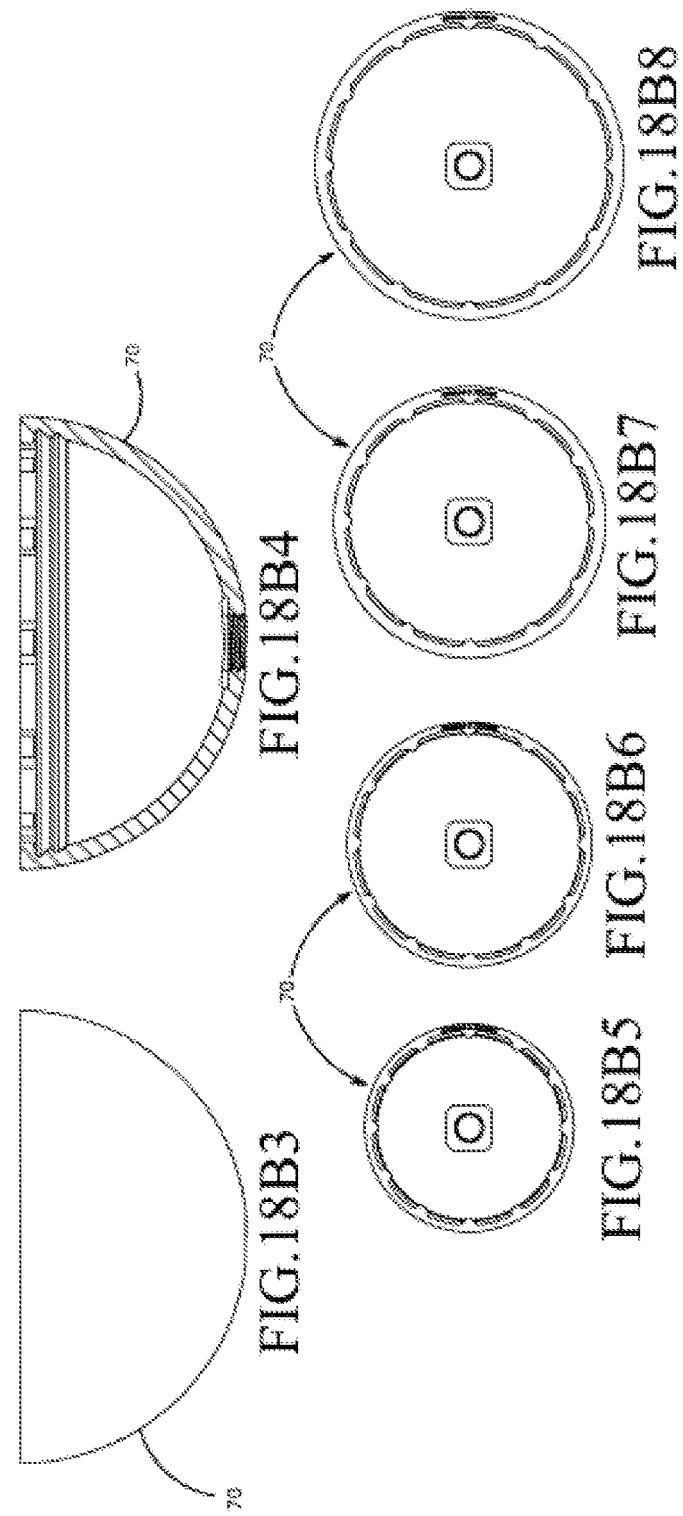

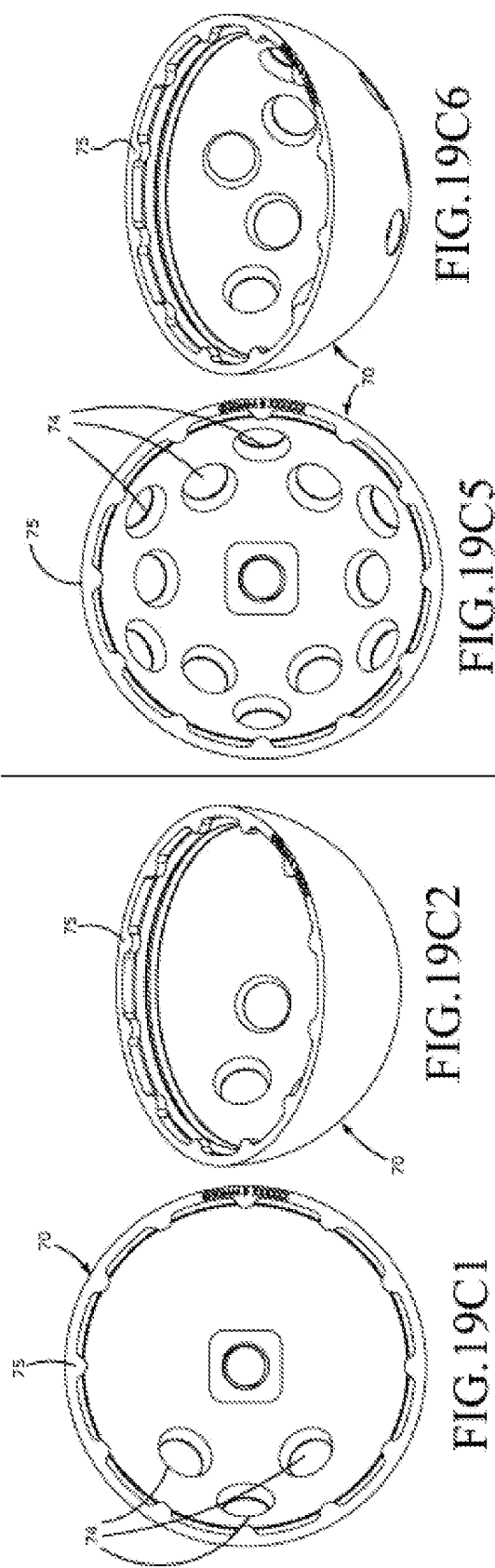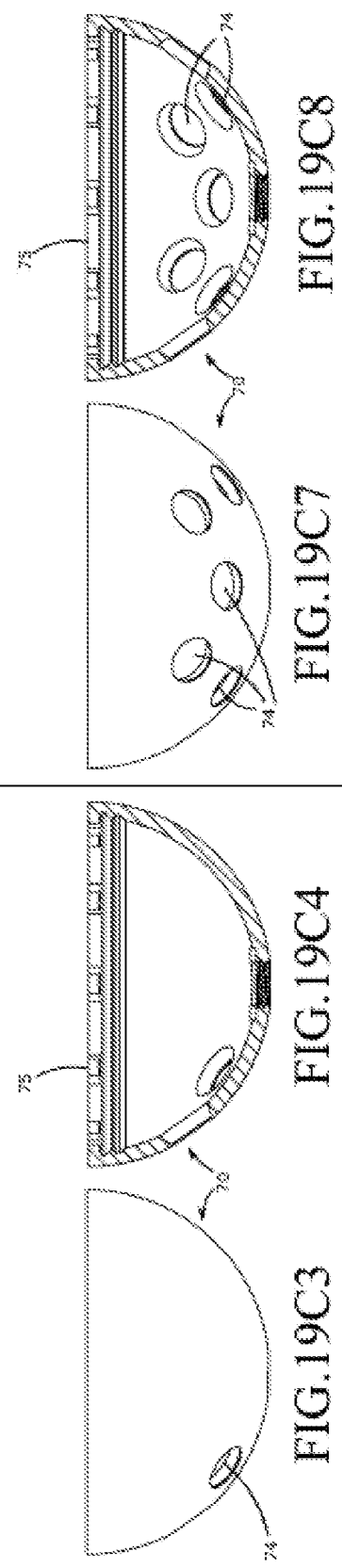

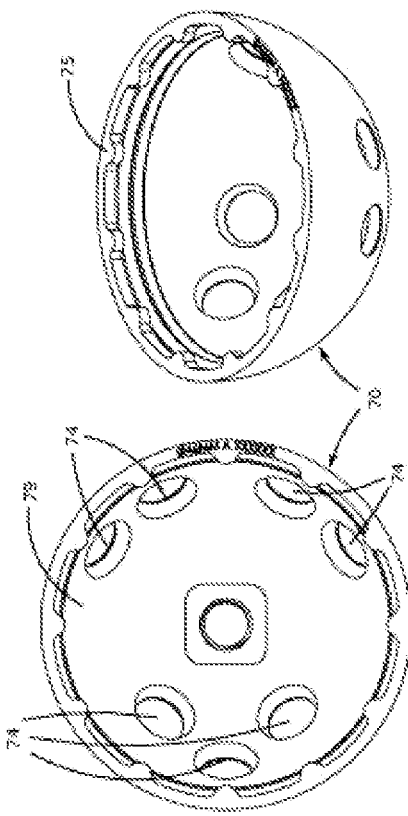
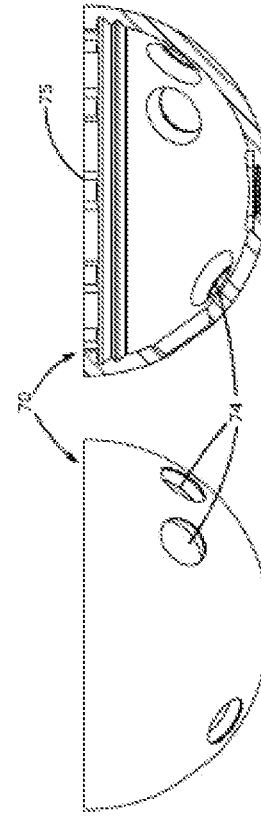
FIG.19C13　FIG.19C14
FIG.19C15　FIG.19C16
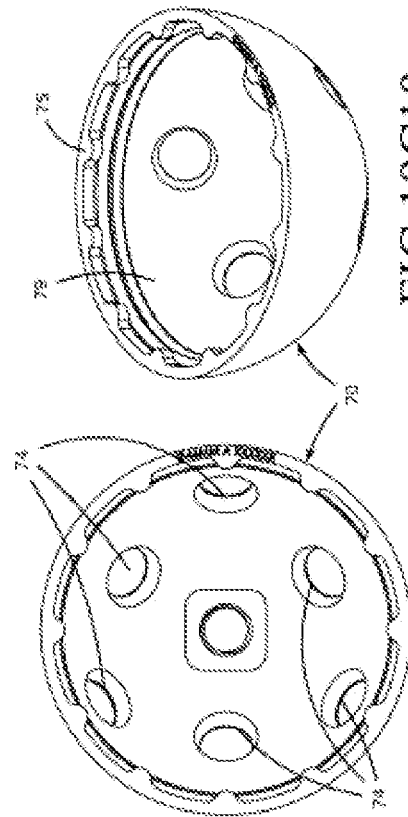
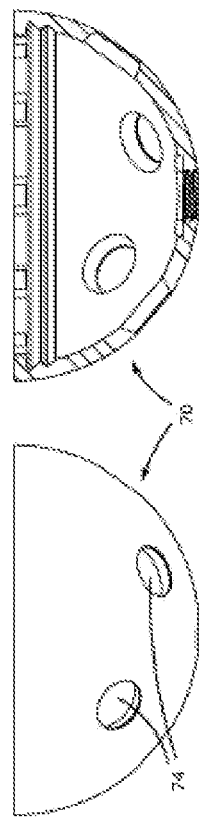
FIG.19C9　FIG.19C10
FIG.19C11　FIG.19C12

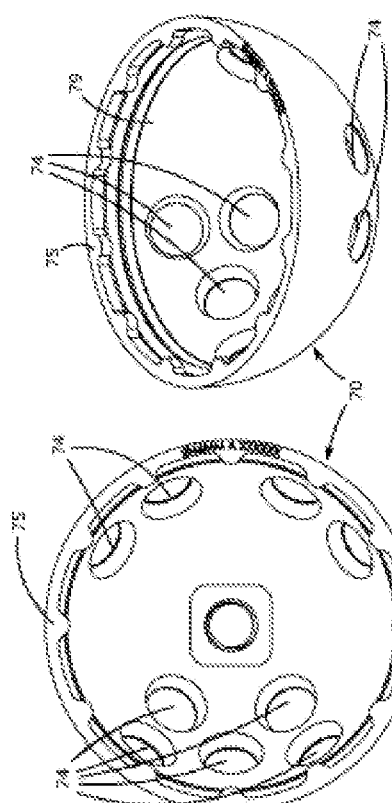
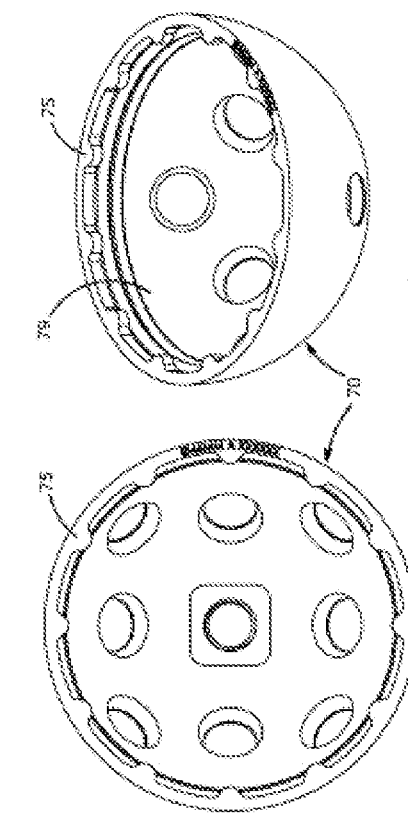
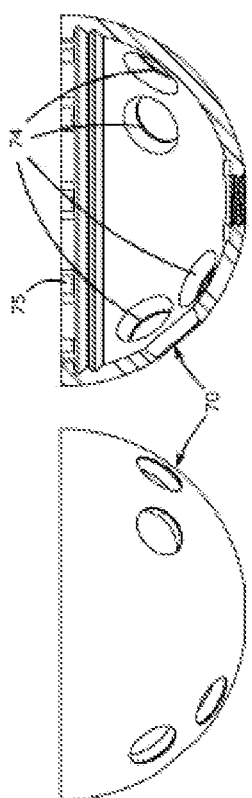
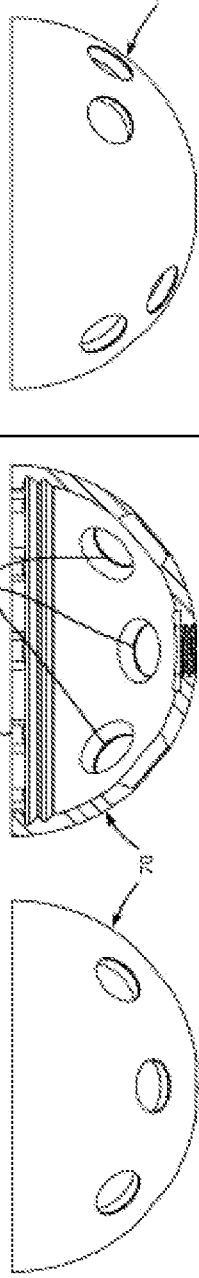
FIG.19C17
FIG.19C18
FIG.19C19
FIG.19C20
FIG.19C21
FIG.19C22
FIG.19C23
FIG.19C24

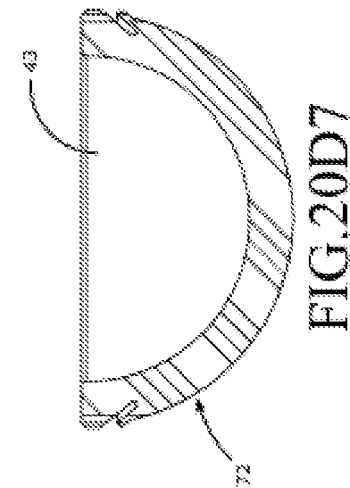
FIG.20D7
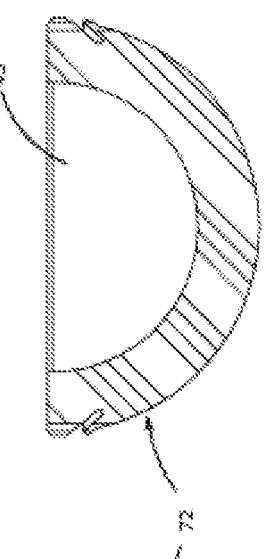
FIG.20D2
FIG.20D4
FIG.20D6
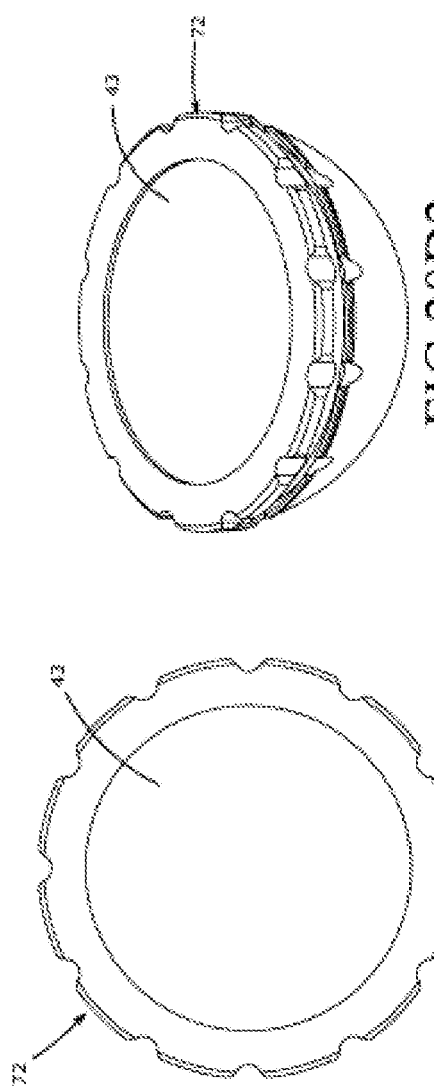
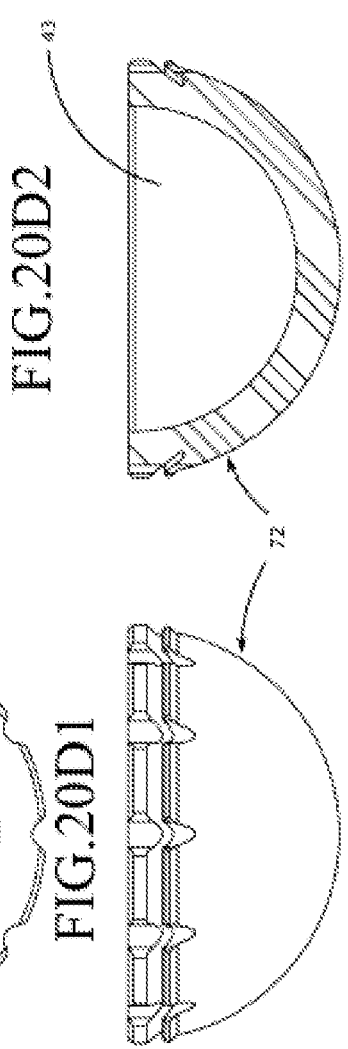
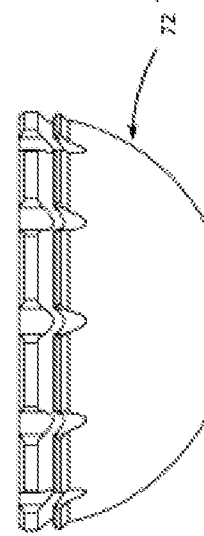
FIG.20D1
FIG.20D3
FIG.20D5

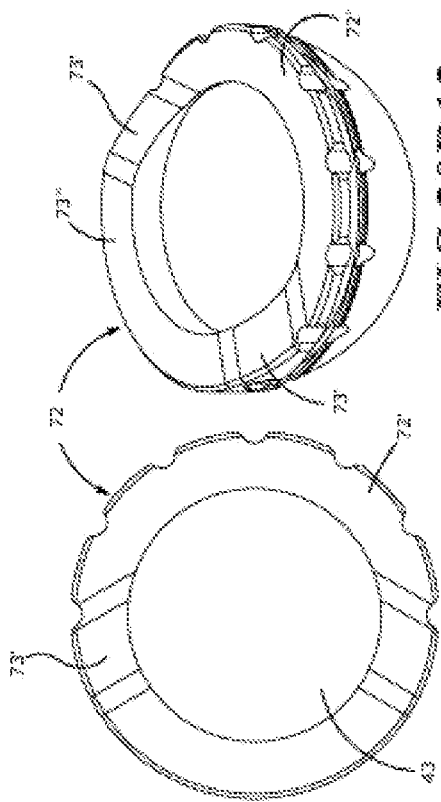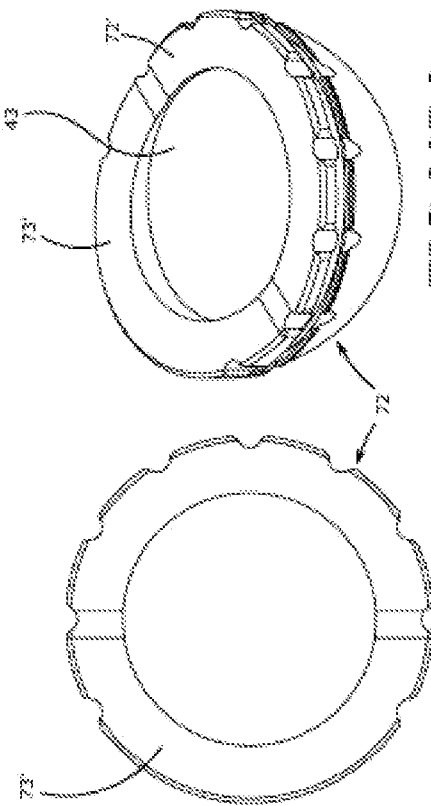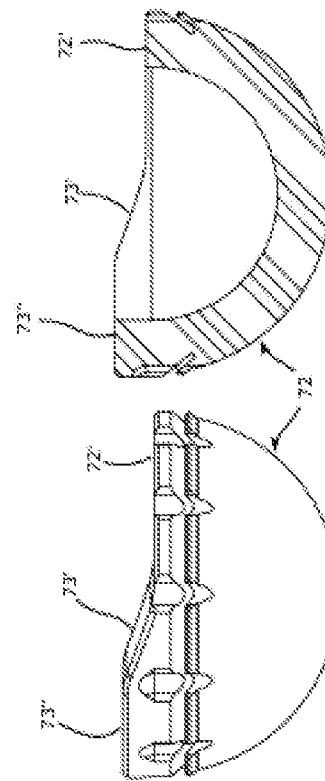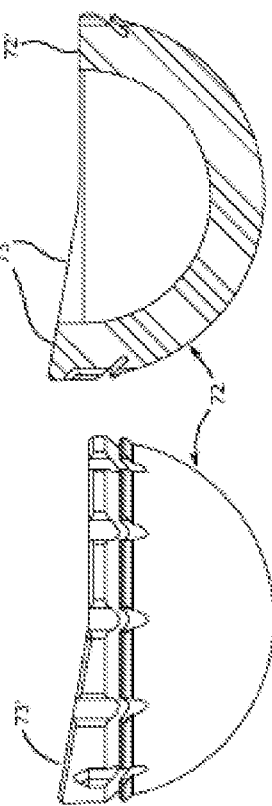

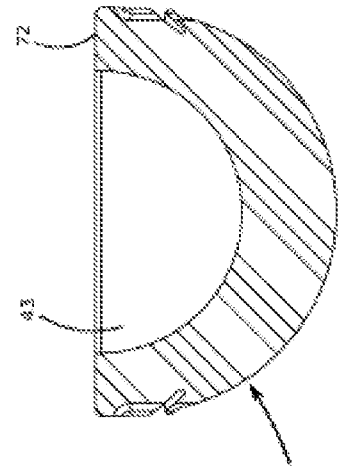
FIG.20D20
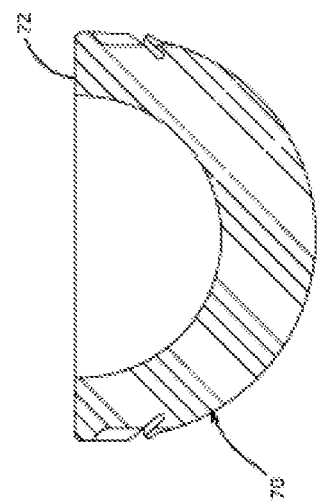
FIG.20D17
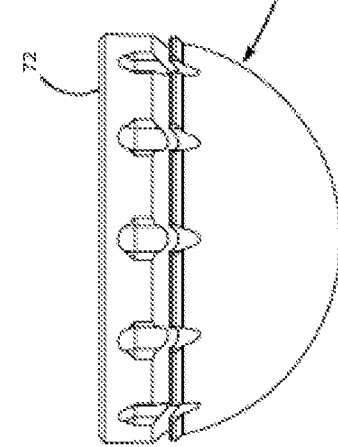
FIG.20D19
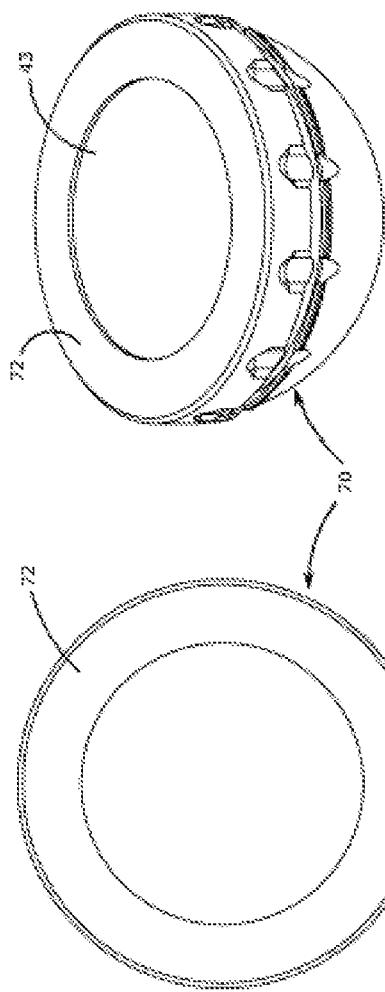
FIG.20D16
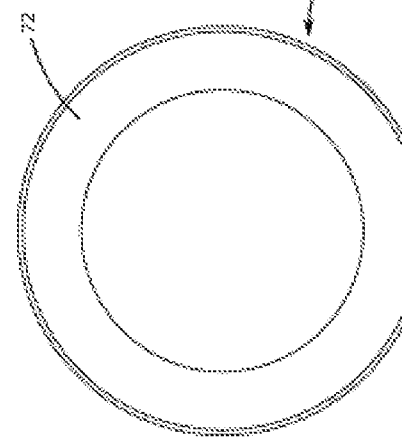
FIG.20D18

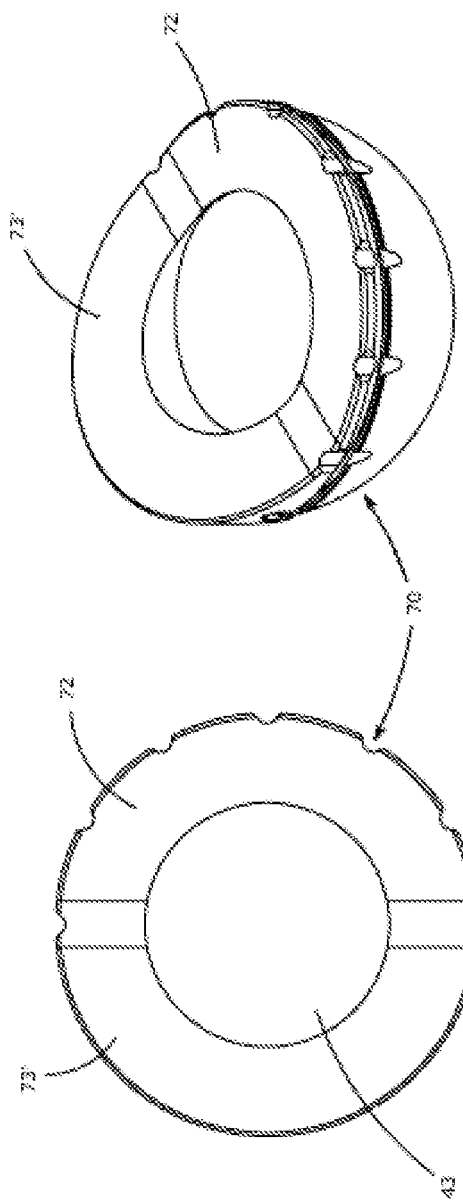
FIG.20D21
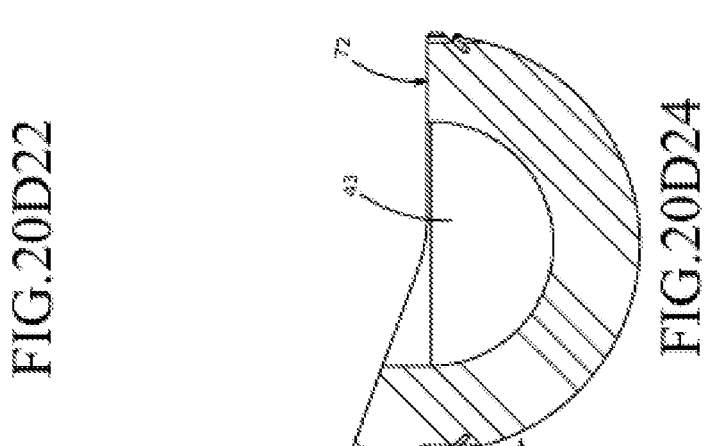
FIG.20D22
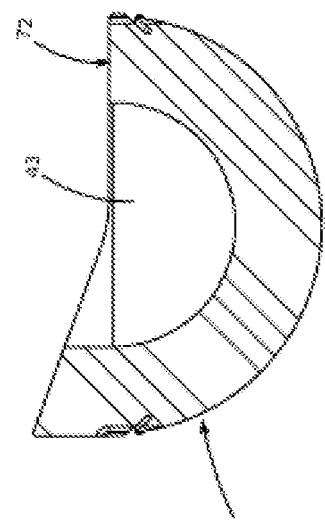
FIG.20D24
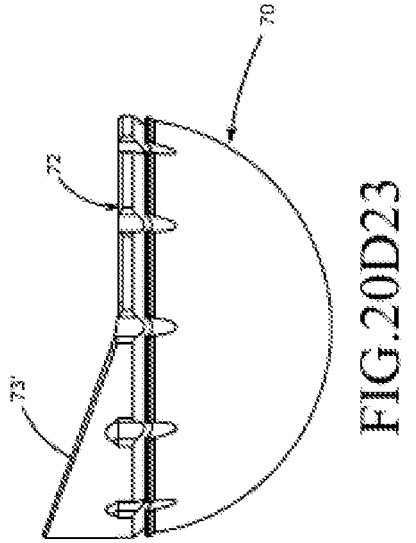
FIG.20D23

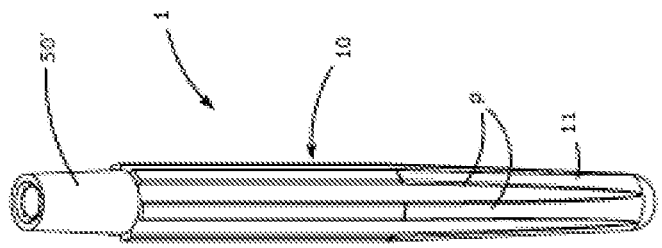
FIG.21E4
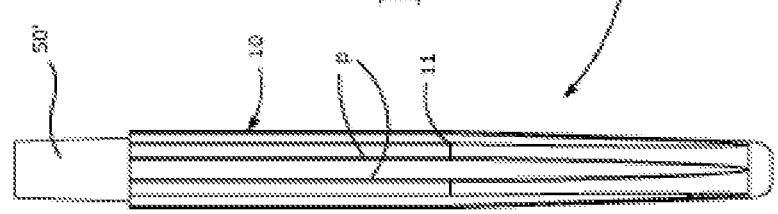
FIG.21E3
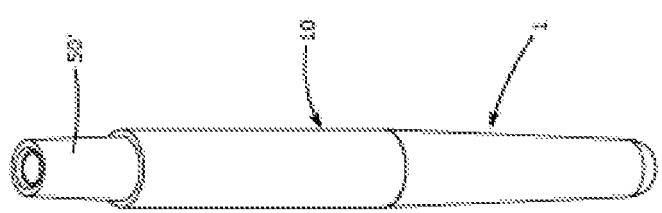
FIG.21E2
FIG.21E1

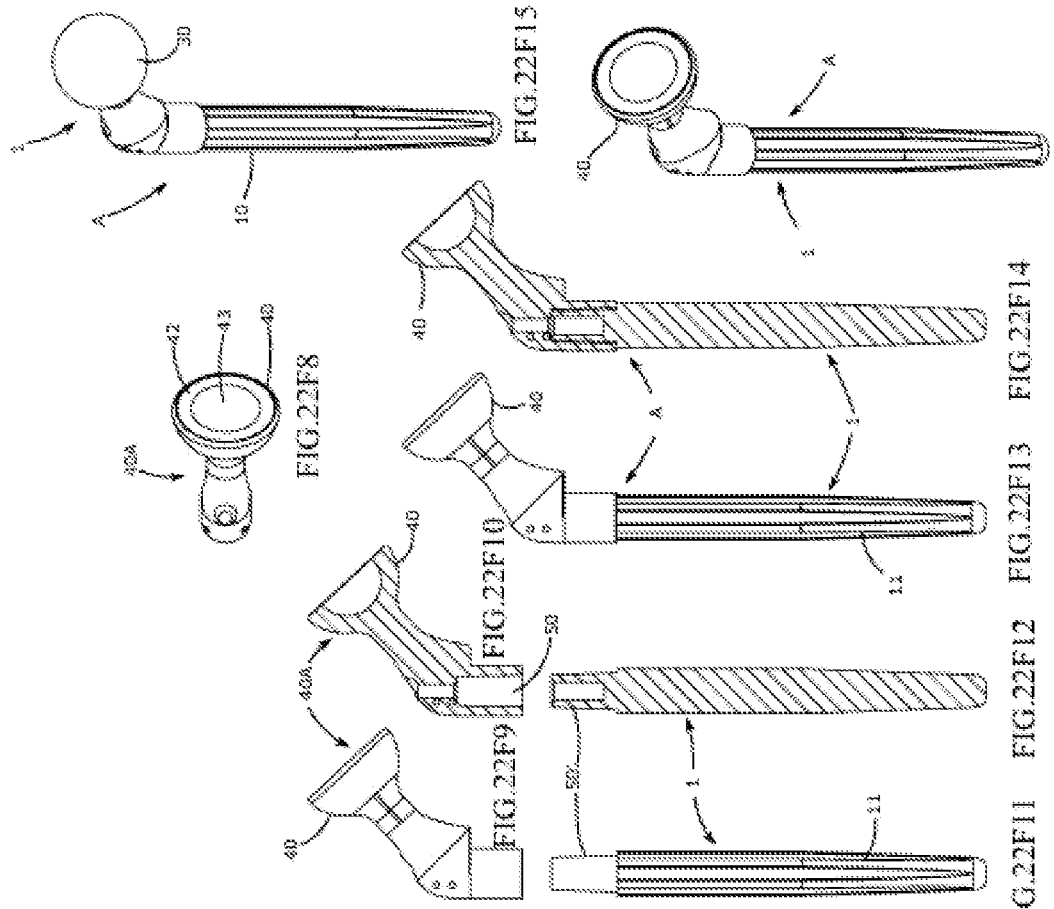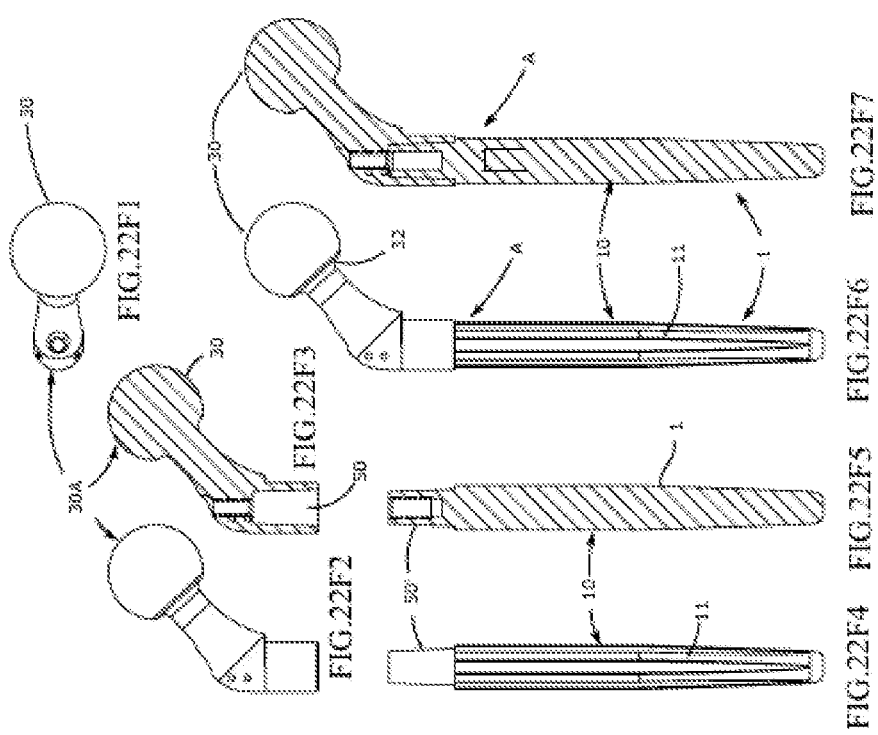

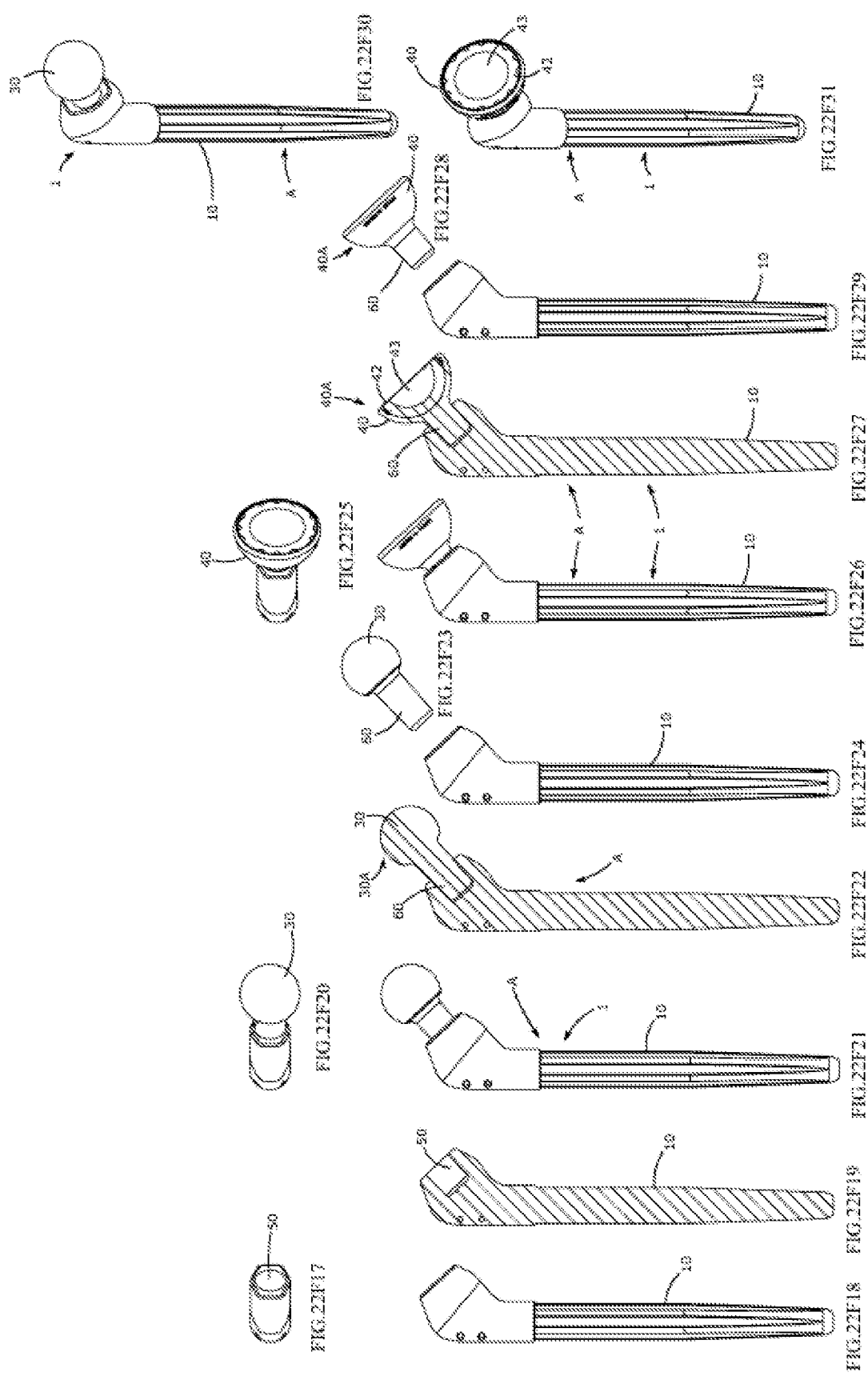

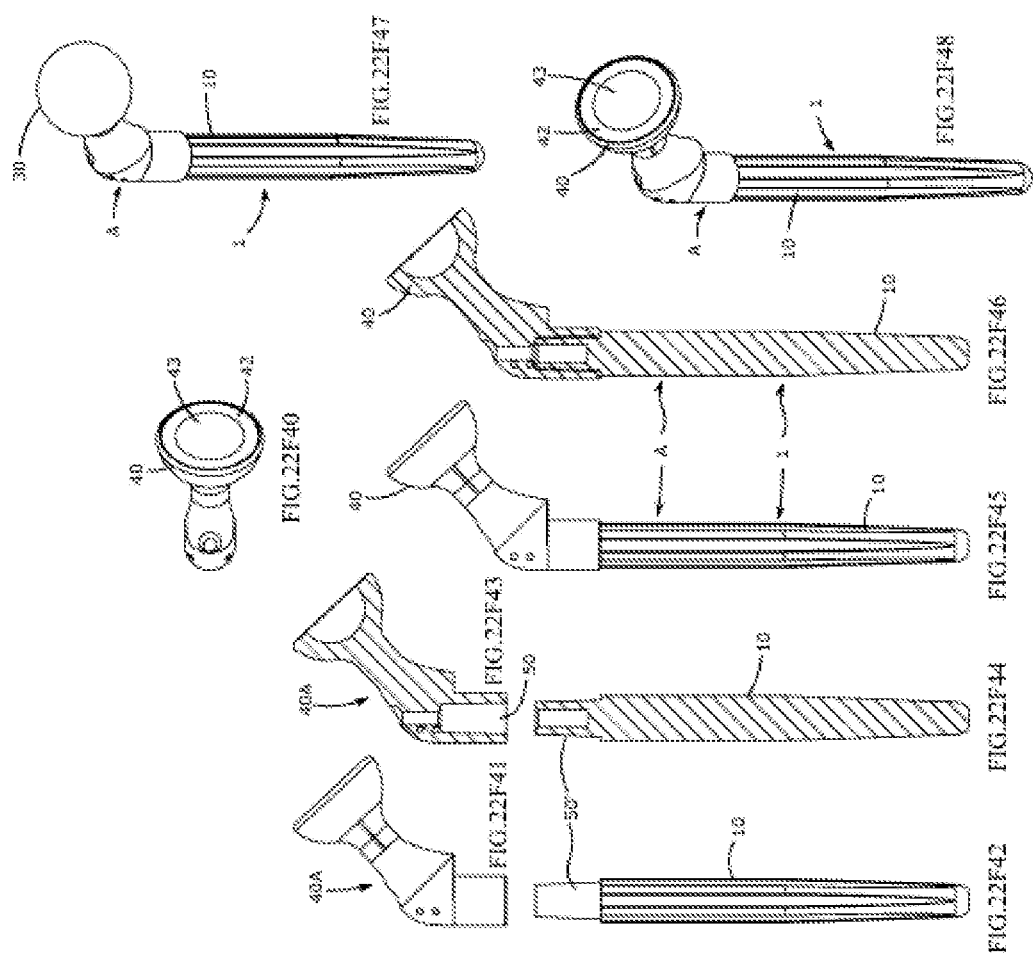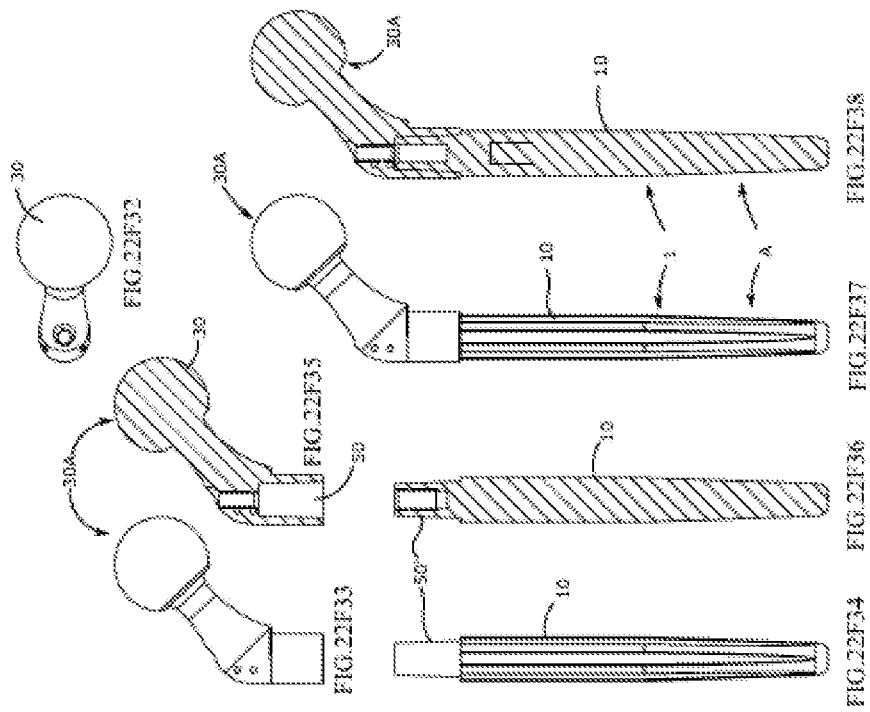

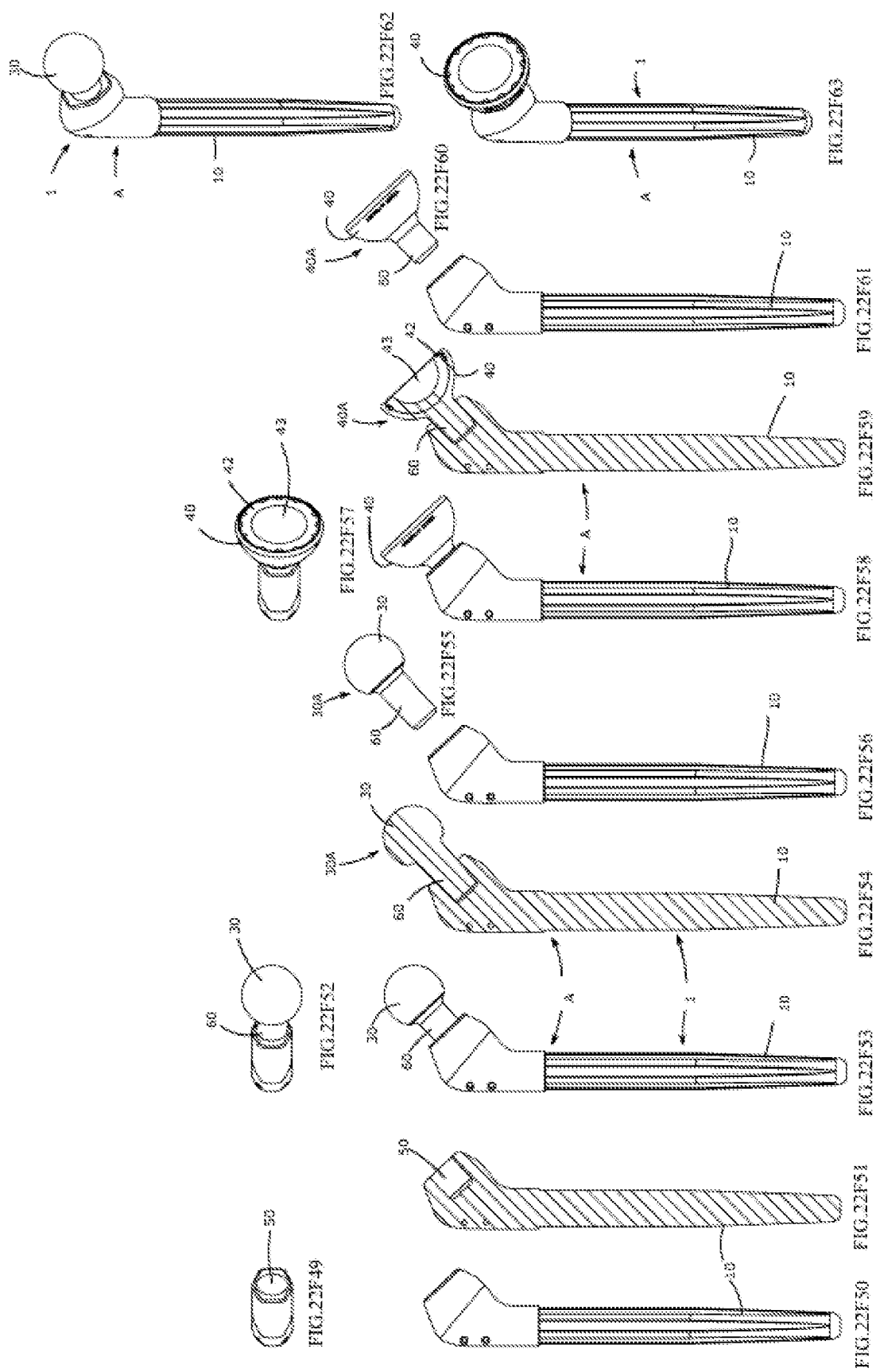

RECONFIGURABLE HIP PROSTHESIS, METHOD OF USE AND KIT

This application claims the priority benefit of U.S. Ser. No. 62/509,304 filed 22, May 2017; the entirety of that application is herein incorporated by reference thereto.

The present invention relates to a reconfigurable hip joint prosthesis and elements therefor which is adapted to be surgically implantable in a human body, a part in the upper femur, another part in the pelvis. The implantable prosthesis may be configured in a reversible manner, and provide alternative configurations as may be desired or necessary. In a further aspect the present invention also includes a method of implanting into a human body a prosthesis as described herein, and subsequently reconfiguring the prosthesis as may be desired or necessary. A still further aspect of the invention is a kit of component elements used in providing a configured implantable prosthesis.

A surgically implantable hip prosthesis typically comprises two major parts, a femoral implant and an acetabular cup. Femoral implant is in part embedded in the upper end of the femur while the acetabular cup is implanted in the acetabulum or other part of the pelvis. These two elements necessarily comprise a meeting surface at an interfacial surface between the femoral implant and the acetabular cup. Such transmits the load of the body through the prosthesis. Typically this is a smooth surface which allows for the physical translation these two elements with respect to one another. A good interfacial surface ensures that the load of a torso of the upper regions of the human body are effectively transferred to the femur of the femoral implant and the acetabular cup, but at the same time does not unduly compromise the available degrees of motion, or of rotation, of the femoral implant (and the femur) relative to the pelvis.

One type of surgically implantable hip prosthesis is wherein the femoral implant includes a stem or shaft having a part which is embedded within a femur, and which has extending therefrom a ball (or similarly configured three-dimensional geometric surface). The hip prosthesis also includes a complementary acetabular cup implantable in a pelvis which comprises a cavity or a socket which contacts a part of the ball (or the similarly configured three-dimensional geometric body) which extends from the stem or shaft of the femoral implant. The interfacial surface is defined between the ball and the acetabular cup when such are in contact with each other. Such are known to the art, e.g.: U.S. Pat. Nos. 5,462,563, 8,323,346 and 9,005,306.

Improved types of implantable hip prostheses are also known, and these are sometimes referred to as "reverse cup" types. In such types, the femoral implant includes a stem or shaft having a part which is embedded within a femur, and which has extending therefrom a femoral cup, which comprises a cavity or a socket. The hip prosthesis also includes a complementary acetabular cup implantable in a pelvis which acetabular cup includes a ball (or similarly configured three-dimensional geometric surface) at least partially present therein. The interfacial surface is defined between the cavity or socket of the femoral cup, and the ball of the acetabular cup when in contact with each other. Such are also known to the art, e.g.: U.S. Pat. Nos. 8,313,531, 8,845,743, 8,992,627, 9,119,724.

In one aspect the invention provides a reconfigurable hip joint prosthesis and elements (or parts) therefor which is adapted to be surgically implantable in a human body, a part in the upper femur, another part in the pelvis.

In a further aspect the reconfigurable hip joint prosthesis has a femoral insert which includes at a proximal end thereof a recess adapted to removably receive a shank of femoral ball element, or the shank of a femoral cup element.

In a further aspect the reconfigurable hip joint prosthesis has a femoral insert which includes at a proximal end thereof a tapered shank which is adapted to be removably received within a recess forming part of a femoral ball element, or within a recess forming part of a femoral ball cup element.

In another aspect of the invention there is provided a method of implanting into a human body a prosthesis as described herein, and subsequently reconfiguring the prosthesis as may be desired or necessary. Reconfiguration may take place external to a human body, or internal to a human body.

In a still further aspect the present invention includes a kit of component parts used in providing one or more parts of, or all parts, required for a reconfigurable hip joint prosthesis as described herein.

Further aspects of the invention will become apparent from the specification, claims and drawings of this patent application.

FIGS. 1A-1C depict an embodiment of a reconfigurable hip joint prosthesis and elements therefor which is adapted to be surgically implantable in a human body, which includes a first embodiment of an acetabular cup and liner and a first embodiment of a femoral ball element; FIG. 1B being a cross-sectional view of FIG. 1A, and FIG. 1C being a cross-sectional view of a part of the reconfigurable hip joint prosthesis to provide more detail of parts of the acetabular cup and liner and the embodiment of a femoral ball element.

FIGS. 2A-2C depict another embodiment of a reconfigurable hip joint prosthesis and elements therefor which is adapted to be surgically implantable in a human body, which includes a second embodiment of an acetabular cup and liner and a second embodiment of a femoral ball element; FIG. 2B being a cross-sectional view of FIG. 2A, and FIG. 2C being a cross-sectional view of a part of the reconfigurable hip joint prosthesis to provide more detail of parts of the acetabular cup and liner and the embodiment of a femoral ball element.

FIGS. 3A-3C depict another embodiment of a reconfigurable hip joint prosthesis and elements therefor which is adapted to be surgically implantable in a human body, which includes a third embodiment of an acetabular cup and liner and a third embodiment of a femoral ball element; FIG. 3B being a cross-sectional view of FIG. 3A, and FIG. 3C being a cross-sectional view of a part of the reconfigurable hip joint prosthesis to provide more detail of parts of the acetabular cup and liner and the embodiment of a femoral ball element.

FIG. 4A and its cross-sectional view of FIG. 4B illustrate a side view a femoral implant.

FIGS. 5A, 5C and its cross-sectional view of FIG. 5B illustrate a side view of an embodiment of a femoral implant and a femoral ball element.

FIGS. 6A, 6B and 6C illustrate side elevational views of different embodiments of femoral ball elements.

FIGS. 7A and B depict an alternative configuration of a femoral implant comprising a femoral stem and affixable femoral ball element.

FIGS. 7C and 7D depict an a further embodiment of a reconfigurable hip joint prosthesis and elements therefor.

Figure 11A:
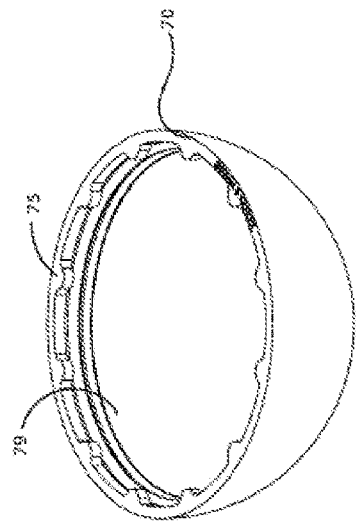
Figure 11B:
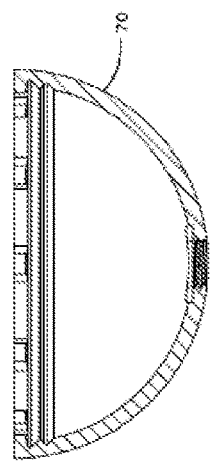
Figure 11C:
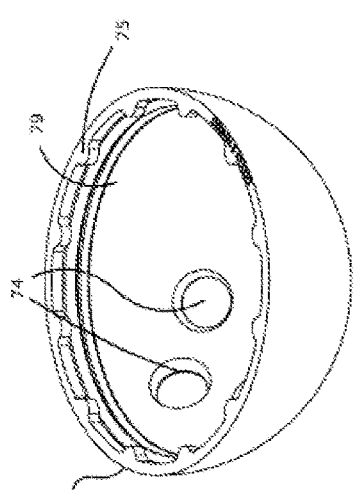
Figure 11D:
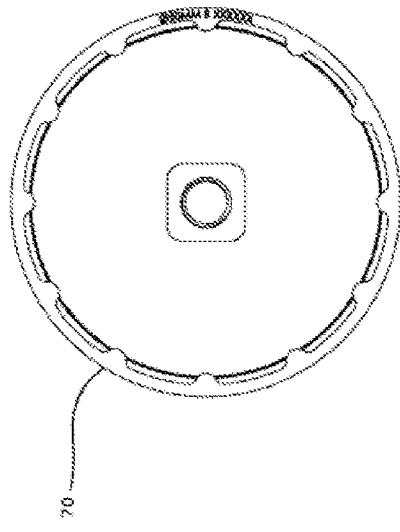
Figure 12A:
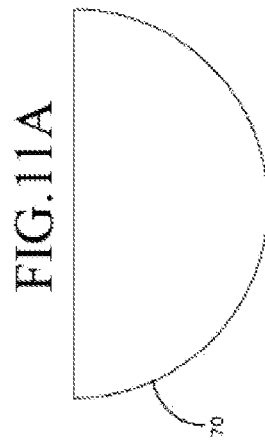
Figure 12B:
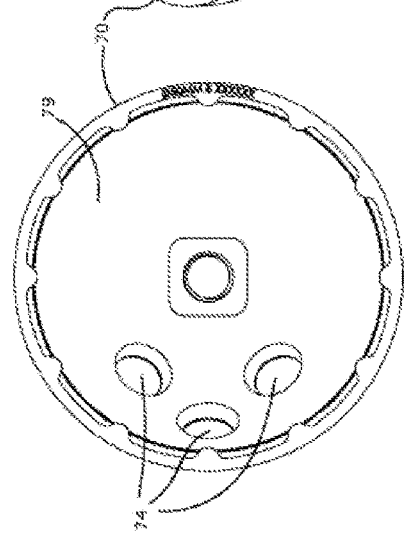
Figure 13B:
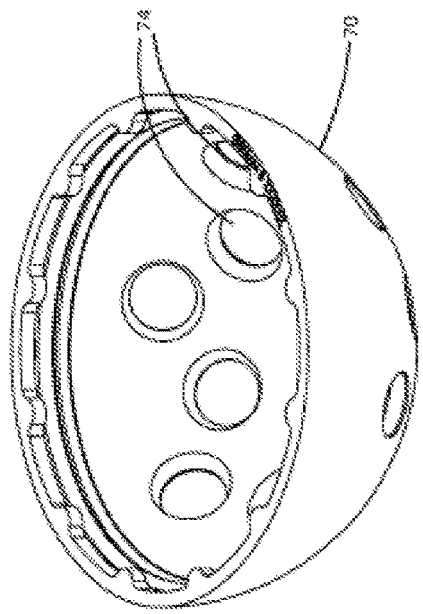
Figure 13A:
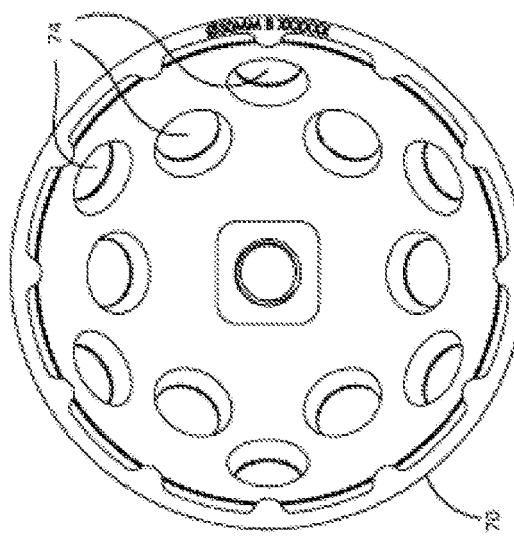

FIGS. 11A, 11B, 11C and 11D, respectively, depict: a top plan view of the interior of, a side perspective view of the interior of, and elevation view, and a cross-section view of an embodiment of an acetabular cup, FIGS. 12A and 12B illustrate a top plan view and a side perspective view of a further embodiment of an acetabular cup, FIGS. 13A, 13B illustrate a top plan view and a side perspective view of a further embodiment of an acetabular cup.

Figure 14B:
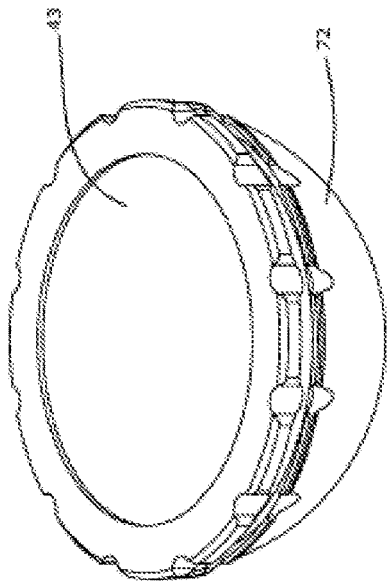
Figure 14A:
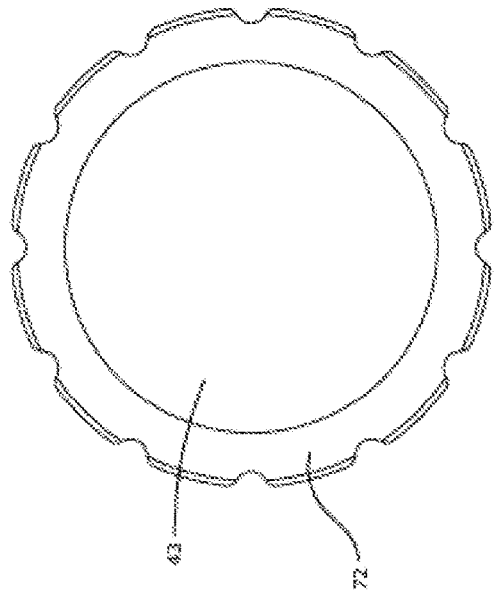

FIGS. 14A and 14B, depict an embodiment of an acetabular cup liner.

Figure 15A:
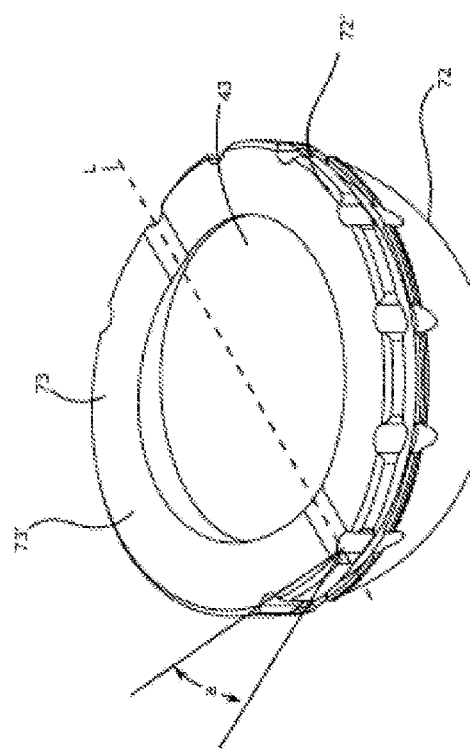
Figure 15B:
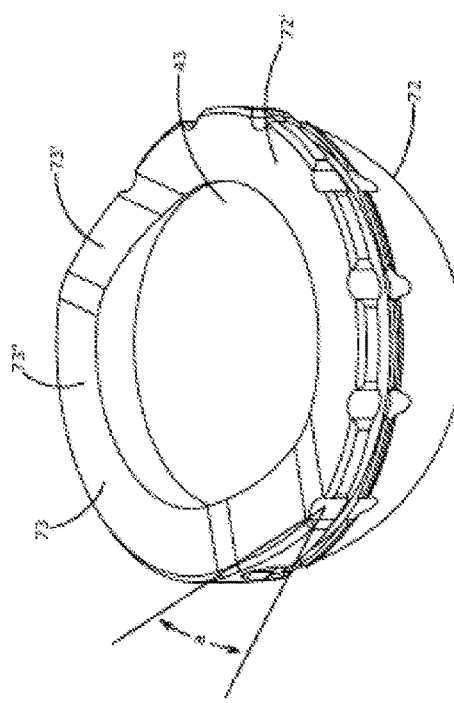

FIGS. 15A and 15B, depict a second embodiment of an acetabular cup liner.

Figure 16A:
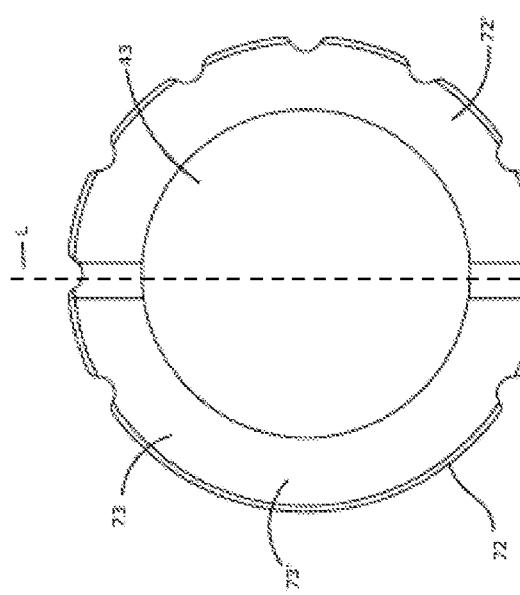
Figure 16B:
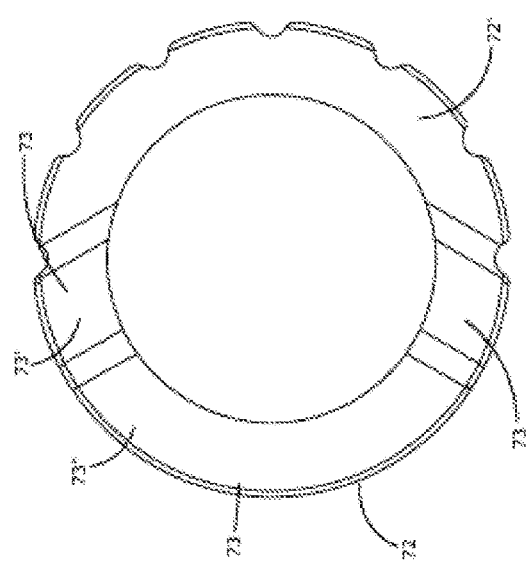

FIGS. 16A and 16B, depict a third embodiment of an acetabular cup liner.

FIGS. 17A1-17A9 depict in elevational view various embodiments of femoral ball elements of different dimensions and configurations; with FIG. 17A4 providing a perspective view of an embodiment of a femoral ball element.

Figure 8:
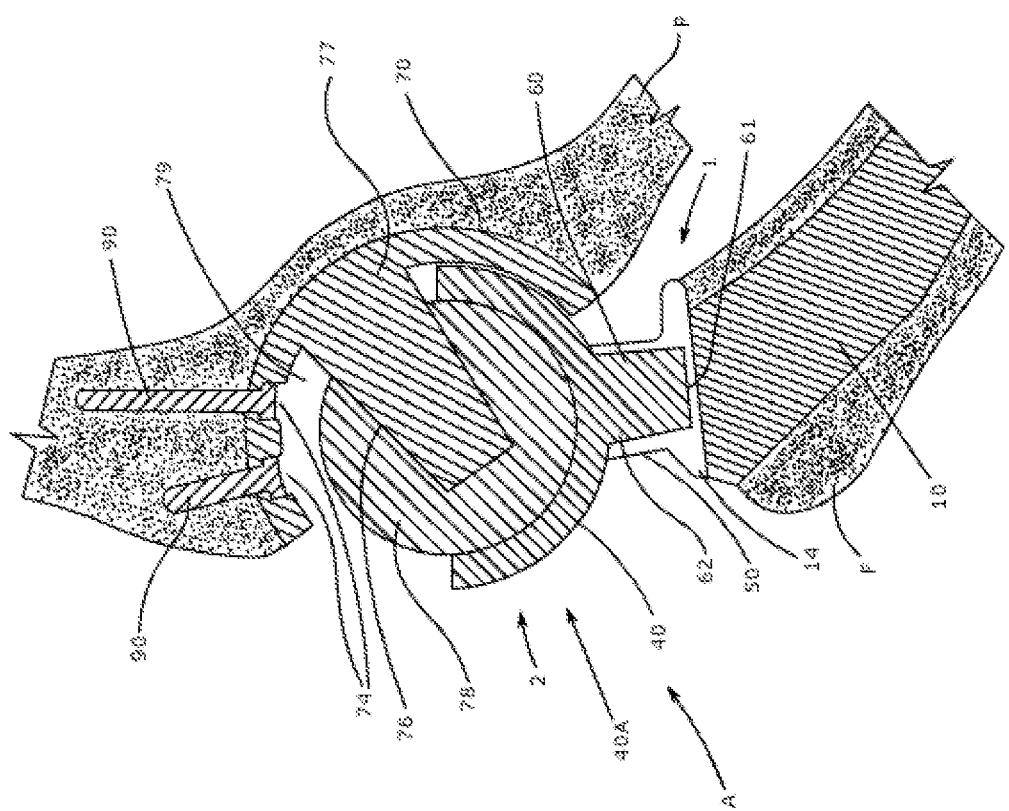
FIG. 8 illustrates in a cross-sectional view an implanted reconfigurable hip joint prosthesis and elements according to an embodiment of the invention which utilizes a femoral cup affixed to the femoral stem, and an acetabular ball removably affixed to the acetabular cup.

FIGS. 18B1-18B8 depict in several views embodiments of acetabular cup elements of different dimensions and configurations; with FIG. 18B4 providing a cross-sectional view of an acetabular cup element. The depicted acetabular cup elements are adapted to be used with an acetabular cup liner.

FIGS. 19C1-19C4 depict in several views an acetabular cup comprising three through holes; FIG. 19C4 is a cross-sectional view thereof.

FIGS. 19C5-19C8 depict in several views of a further embodiment of an acetabular cup comprising twelve through holes; FIG. 19C8 is a cross-sectional view thereof.

FIGS. 19C9-19C12 depict in several views of a yet further embodiment of an acetabular cup comprising six through holes; FIG. 19C12 is a cross-sectional view thereof.

FIGS. 19C13-19C16 depict in several views of a yet further embodiment of an acetabular cup comprising seven through holes; FIG. 19C16 is a cross-sectional view thereof.

FIGS. 19C17-19C20 depict in several views of a yet further embodiment of an acetabular cup comprising six through holes; FIG. 19C20 is a cross-sectional view thereof.

FIGS. 19C21-19C24 depict in several views of a yet further embodiment of an acetabular cup comprising nine through holes; FIG. 19C24 is a cross-sectional view thereof.

FIGS. 20D1-20D2 depict in several views an embodiment of an acetabular cup liner; FIG. 20D3 provides a side view thereof, and FIG. 20D4 provides a cross-sectional view thereof.

FIGS. 20D5, 20D6 and 20D7 depict in cross-sectional views various acetabular cup liners; each of these have differently dimensioned acetabular cup liner recess 43.

FIGS. 20D8-20D11 depict in several views a further embodiment of an acetabular cup liner; FIG. 20D11 provides a cross-sectional view thereof.

FIGS. 20D12-20D15 depict in several views a still further embodiment of an acetabular cup liner; FIG. 20D15 provides a cross-sectional view thereof.

FIGS. 20D16-20D20 provide several views of a further embodiment of an acetabular cup liner; FIGS. 20D19 and 20D20 provides a cross-sectional view thereof.

FIGS. 20D21-20D24 depict in several views a still further embodiment of an acetabular cup liner; FIG. 20D24 provides a cross-sectional view thereof.

FIGS. 21E1 and 21E2 illustrate in two views an embodiment of a femoral stem element.

FIGS. 21E3 and 21E4 illustrate in two views an embodiment of a femoral stem element having surface flutes.

FIGS. 22F1-22F7 depict in various views elements of a first embodiment of a reconfigurable hip joint prosthesis and elements therefor comprising an acetabular ball element.

FIGS. 22F8-22F14 and 22F16 depict in various views elements of a further embodiment of a reconfigurable hip joint prosthesis and elements thereof comprising a femoral cup element.

FIG. 22F15 depicts a further embodiment of a reconfigurable hip joint prosthesis and elements thereof comprising a further acetabular ball element.

FIGS. 22F17-22F24, 22F30 depict in various views elements of another embodiment of a reconfigurable hip joint prosthesis and elements therefor having a femoral ball element 30A.

FIGS. 22F25-22F29 and 22F31 depict in various views elements of another embodiment of a reconfigurable hip joint prosthesis and elements thereof comprising a femoral cup element and a femoral stem element having a fluted sidewall.

FIGS. 22F32-22F38, and 22F47 depict in various views elements of another embodiment of a reconfigurable hip joint prosthesis and elements thereof having a femoral ball element and a femoral stem element having a smooth sidewall.

FIGS. 22F42-22F46 and 22F48 which depict in various views elements of another embodiment of a reconfigurable hip joint prosthesis and elements therefor comprising a femoral cup element and a femoral stem 10 element having smooth sidewalls.

Figs. 22F40 and 22F41 depicts an embodiment of a femoral cup element 40 affixable to a femoral stem 10.

FIGS. 22F49-22F56 and 22F62 which depict in various views elements of another embodiment of a reconfigurable hip joint prosthesis and elements thereof having a femoral cup element 40A and a femoral stem 10 element having smooth sidewalls.

FIGS. 22F57-22F61 and 22F63 which depict in various views elements of another embodiment of a reconfigurable hip joint prosthesis and elements thereof, having a femoral cup element and a femoral stem element.

The femoral implant includes a femoral stem which may be any element, article or device which is suitable to be inserted within a portion of a femur, and may you include as a part of its construction a detachable femoral ball or a detachable femoral cup, or alternately may be adapted to receive a femoral ball or a femoral cup which may be interchanged as necessary or desired.

The latter configuration of a femoral femoral implant allows for the reconfiguration of the femoral implant to include either a femoral ball or a femoral cup (described in more detail hereinafter) and is a preferred embodiment permits for an implanted femoral implant to be reconfigured from a first (viz., initial) configuration to a second (viz., alternate) configuration without requiring the removal of the implanted femoral stem from the femur. For example, a first configuration may be wherein the femoral implant includes an implantable femoral stem part and femoral ball (or a different configured three-dimensional geometric surface), and a complementary acetabular cup implantable in a pelvis which comprises a cavity or a socket which contacts a part of the femoral ball. The cavity or socket is frequently present in an acetabular cup liner which may be affixed to or form part of the acetabular cup, which acetabular cup liner is usually fabricated of a polymeric or ceramic material. The cavity or socket includes a surface which complements the femoral ball (or the different configured three-dimensional geometric surface). Another, alternative or second configuration may be wherein the femoral implant includes an implantable femoral stem part and a femoral cup which comprises a cavity or a socket, and a complementary acetabular cup implantable in a pelvis which complementary acetabular cup comprises a ball (or a different configured three-dimensional geometric surface) at least partially present therein. Again, the cavity or socket is frequently present in an acetabular cup liner which may be affixed to or form part of the acetabular cup, and is usually fabricated of a polymeric or ceramic material. The cavity or socket includes a surface which complements the ball (or a different configured three-dimensional geometric surface) forming part of the acetabular cup. According to this preferred embodiment, the configuration of the femoral implant can be altered between the first configuration described, and the second configuration described, as well as vice-versa without requiring removal of the femoral stem from the femur. Such provides a reconfigurable hip joint prosthesis, which is particularly advantageous, as reducing the extent of required surgery to effectuate such change in the form of the hip joint prostheses. Such a reconfigurable hip joint prosthesis, permits for a surgeon a greater latitude of options during hip replacement therapy as allowing for the surgeon to determine, either prior to but more advantageously subsequently to the implantation of a femoral stem an appropriate configuration of the femoral implant best suited for patient's needs, as the surgeon may then choose the optimal configuration of the femoral implant, e.g, which may be a first configuration, or a second configuration as described herein. Thus, when the necessary component parts or elements are provided and/or made available to the surgeon in the operating room (or operating theater), such as in the form of one or more kits of component parts or elements from which an implantable reconfigurable hip prosthesis according to either a first configuration or second configuration are provided to or made available to the surgeon, the surgeon may use the component parts or elements to provide an optimal configuration to meet the patient's needs by assembling a suitable implantable hip joint prosthesis. The surgeon is thus not constricted to use an implantable hip prosthesis according to a single configuration of a prosthesis as is prevalent in the prior art, as the reconfigurable hip joint prosthesis of the present invention allows for elements thereof to be switched without the need to remove the femoral stem from the femur, as the reconfigurability of the various elements allows for a first configuration or a second configuration of a reconfigurable hip joint prosthesis to be provided to the patient. Additionally, such a reconfigurable hip joint prosthesis permits for surgeon, after an initial or prior surgery wherein a hip prosthesis was previously implanted, to effectuate the reconfiguration of the hip joint prosthesis, e.g, to "convert" it from a first configuration to a second configuration, or from a second configuration to a first configuration, without requiring removal of the previously implanted femoral implant, as the either a femoral ball or a femoral cup can be detached from a part of the femoral stem extending beyond the femur and interchanged within the patient's body, without requiring the removal of the implanted part of the femoral implant from the femur. Such may be thus useful in so-called 'revision surgery' wherein a prior implanted hip prosthesis is reconfigured, as described herein, especially from a first configuration to a second configuration, or vice a-versa. A reconfigurable hip joint prosthesis as provided herein reduces the surgical trauma typically associated with removal of an implanted femoral implant or a femoral stem and replacement with further femoral implant, which in the prior art is often referred to as a revision stem. Such also reduces the post-operative recovery period required of the patient. The provision of a reconfigurable femoral implant as described herein, which includes detachable elements or parts, allows for the in vivo reconfiguration of the a reconfigurable hip joint prosthesis within the patient, and allows for a revision surgery to be undertaken without necessitating the use of a further femora implant or removal of the previously implanted femoral stem.

Thus, amongst the aspects of the invention there is also included a method of implanting into a human body a reconfigurable hip joint prosthesis as described herein, and subsequently reconfiguring the reconfigurable hip joint prosthesis as may be desired or necessary. More particularly the method includes the steps of altering the configuration of an implanted femoral implant between a first configuration described, and a second configuration described. Still further the reconfiguration may be undertaken without removal of the previously implanted femoral stem.

Amongst the further aspects of the invention is included a kit of component parts used in providing a configured implantable prosthesis as described herein. The kit necessarily includes an implantable femoral implant which may be reconfigured to receive a femoral ball in a part thereof, viz. may be attached to a femoral stem part, or alternately to receive a femoral cup in a part thereof, viz. may be attached to a femoral stem part wherein an installed femoral ball may be removed, and interchanged with a femoral cup, as well as vice a-versa. Preferably the femoral ball and femoral cup parts of a femoral implant may be interchanged with a femoral stem part external to a human body, but preferably is also interchangeable within a human body without requiring withdrawal of a previously implanted femoral stem already present within the femur. Optionally, but very advantageously the kit also includes at least one femoral ball, and at least one femoral cup, but preferably a plurality of femoral balls and/or femoral cups are also provided as a part of the kit. In such manner, a surgeon may, in the operating room, assemble a suitable femoral implant comprising a femoral stem, and an installed femoral ball or in the alternative, an installed femoral cup. Additionally, the kit may comprise further component parts necessary to assemble a complete reconfigurable hip joint prosthesis, such as one or more acetabular cups having differing configurations, or which are configurable to be complementary with an implanted, or implantable femoral stem, and any tools, guides, or ancillary devices, or apparatus which is useful in implanting, removal, or modification or one or more parts of the reconfigurable hip joint prosthesis.

Such kits need not necessarily be provided in a unitary package, or as a unitary assemblage of articles but can be divided amongst separate packages which nonetheless, may be used collectively during a surgical operation relating to a hip joint prosthesis described herein. Not all of the component parts or elements of the hip joint prosthesis described herein need necessarily be used, indeed such is unforeseen as typically a plurality of femoral stems, femoral balls, femoral cups, and acetabular cups of different configurations and/or dimensions, may be provided (and advantageously are provided) within an operating theater and/or alternately made available to a surgeon so to facilitate availability of the component parts or elements, and thereby ensuring that they may select an optimal configuration of the implantable hip joint prosthesis, in particular the reconfigurable hip joint prosthesis so to best meet a patient's requirements.

A description of various component parts and elements useful in the implantable hip joint prosthesis, and in the kits and methods of use follows. It is to be understood that the following description is a non-limiting in nature, and that other configurations not particularly discussed or not specifically illustrated in one or more the attached drawing figures, may also be used in conformity with one or more of the aspects of the present invention. Certain of the disclosed drawing figures and configurations discussed represent presently preferred embodiments according to certain aspects of the invention The reconfigurable hip joint prosthesis comprise femoral implants which include femoral stems which typically include a distal end configured to be inserted into a femur and retained therein, and a proximal end which is configured to provide a physical interface with a further part of the implantable hip prosthesis, typically an acetabular cup or part thereof, i.e, an acetabular cup liner. The proximal end may include a removable and reinsertable femoral ball or a removable and reinsertable femoral cup. Femoral stems may monolithic, or may have separable elements which are assembled to form a femoral stem, in a modular fashion. A femoral ball or a femoral cup may be removably affixed to a part of the femoral stem, preferably at or near a distal end or part thereof. A femoral ball or a femoral cup may be already affixed when supplied in a kit, or otherwise provided for use, or a femoral stem may be supplied separately from one or more femoral balls and/or one or more femoral cups, i.e., in a kit containing one or more such component parts.

The femoral ball preferably includes a curved, ball part (or other three-dimensional geometric surface, including non-spherical geometric surfaces) which preferably comprises a substantially hemispherical portion having a radius of between about 5-60 mm, preferably between about 10 mm and 50 mm, and a shank extending outwardly therefrom. Such corresponds to a diameter of between about 10-120 mm, preferably between about 20 mm and 100 mm; most preferably the diameter is not in excess of about 42 mm. However other lengths are also possible and are foreseen to be useful; such may include "nominal lengths" known to the art.

In certain embodiments the femoral ball includes shank at the base or termination of the curved, ball part (or other three-dimensional geometric surface) of the femoral ball and the shank extends outwardly from the base. The shank may be of different lengths and dimensions. Typically, the shank has a length of from about −5 mm to about +25 mm, preferably from about −2 mm to about +12 mm when measured between a distal end of the shank, and the base. The shank may be of any geometric shape, but is advantageously either cylindrical or substantially cylindrical in cross-section as such a geometry facilitates its placement within a femoral stem or other part of a femoral (or other) implant. More advantageously, the shank has a smaller cross section or diameter at its distal end, then at its proximal and closer to the base or the termination of the curved, ball part, and has a surface and/or geometry which is complementary to a cylindrical bore or other recess of a femoral stem such that a close tolerance fit is achieved. Advantageously both the shank and the recess of the femoral stem are tapered.

Commonly the femoral ball is sized according to this radius, and conventional sizes of between about 10 mm and 60 mm, and especially about 22 mm-40 mm are preferred.

In a kit according to the invention, a plurality of femoral balls may be provided, typically having different sizes and preferably also having shanks of different lengths which as noted previously the stem may be tapered.

The shank of a femoral ball or femoral cup which is insertable into the recess of a femoral stem may be a cylindrical bore having consistent cross-section parallel to the central axis of the recess, but is preferably a recess or bore having a larger diameter at its inlet than at the distal end thereof, viz., is tapered. The configuration of the taper may be any which is complementary to the dimensions of the tapered bore or recess of the femoral implant. The angle of the taper relative to a central axis of the shank may vary, but advantageously has an angle of between about 0.5 and 5 degrees of arc, preferably between about 1 and 3 degrees. Conventional configurations of such tapers are preferred, include one or more of: a Morse taper, a Jacobs taper, a Brown & Sharpe taper, a Jarno taper, with a Morse taper, especially Morse tapers having an angle of between about 1 and 3 degrees of arc, preferably having a taper having an angle or, within a range of two or more of the following angles: 0.01°, 0.1°, 0.2°, 0.3°, 0.4°, 0.5°, 0.6°, 0.7°, 0.8°, 0.9°, 1°, 1.1°, 1.2°, 1.3°, 1.4°, 1.5°, 1.6°, 1.7°, 1.8°, 1.9°, 2°, 2.1°, 2.2°, 2.3°, 2.4°, 2.5°, 2.6°, 2.7°, 2.8°, 2.9°, 3°, 3.1°, 3.2°, 3.3°, 3.4°, 3.5°, 3.6°, 3.7°, 3.8°, 3.9°, 4°, 4.1°, 4.2°, 4.3°, 4.4°, 4.5°, 4.6°, 4.7°, 4.8°, 4.9°, 5°.

In the drawing figures, throughout the various views like elements are indicated by like reference numerals and/or letters, unless indicated otherwise.

Examples of femoral implants comprising a femoral stem including a removably affixable femoral ball having a shank extending from the ball part thereof are depicted on FIGS. 1A, 1B, 2A, 2B, 3A, 3B. FIGS. 1C, 2C, and 3C depict cross-sectional views of a detail of a femoral ball and a corresponding acetabular cup.

A reconfigurable hip joint prosthesis A is depicted in FIG. 1A, and its cross-sectional view of FIG. 1B which illustrates in a side view a femoral implant 1 which includes both a femoral stem 10 which tapers outwardly from a distal end 12 to a proximal end or proximal region 14. Present within the proximal region 14 is a tapered recess 50 within which is removably seated the complementary tapered shank 60 which extends outwardly from a base part 32 of a femoral ball 30 as illustrated in the figures. While not shown in the figure, it is to be understood that the femoral ball element 30A, here comprising the femoral ball 30 and shank 60 can be substituted by a femoral cup element which while not shown here, is described in following figures, which femoral cup element also includes a similar complementary tapered shank 60. FIG. 1C shows more detailed view of parts of FIG. 1A, and illustrates an acetabular cup 70 which includes within it an acetabular cup liner 72 including a cavity which is in physical interfacial contact with parts of the hemispherical surface of the femoral ball 30. The hemispherical acetabular cup liner 72 is within the edge 75 of the acetabular cup and is thus contained entirely therein. Also shown is perforation 74 passing through the acetabular cup 70; one or more such perforations are ideally suited for the insertion of fasteners such as a bone screws therethrough, and subsequently the acetabular cup liner 72 can be fitted within the acetabular cup 70. The places of contact, or more accurately the area of interfacial contact between the femoral ball 30 and the acetabular cup liner 72 of the acetabular cup 70 defines an interface between these elements, which are load bearing surfaces and which are slideable a/o rotatable (or otherwise moveable) with respect to each other.

The embodiment of the reconfigurable hip joint prosthesis A illustrated in FIGS. 2A and 2B substantially similar to the views presented in FIGS. 1A and 1B, but differ in the configuration and the dimensions of the femoral ball 30, its shank 60 and as is best seen from the view of FIG. 2C, the dimensions of and configuration of the acetabular cup liner 72 in the femoral cup 70. In particular, in this embodiment is seen that a portion 73 of the acetabular cup liner 72 extends beyond the edge 75 of the acetabular cup 70. The embodiment depicts that the center of the femoral ball 30 is offset by a greater distance from the center of the acetabular cup 70, than in prior FIGS. 1A-1C.

The embodiment of the reconfigurable hip joint prosthesis A shown in FIGS. 3A and 3B substantially similar to the views presented in FIGS. 1A and 1B, but differ in the configuration and the dimensions of the femoral ball 30, its shank 60 and as is best seen from the view of FIG. 3C, the acetabular cup liner 72 in the femoral cup 70. In particular, in this embodiment is seen that a portion 73 of the acetabular cup liner 72 extends beyond all of the edge 75 of the acetabular cup 70.

The depictions of FIGS. 1A, 1B, 1C, 2A, 2B, 2C, 3A, 3B and 3C illustrate one preferred embodiment of a reconfigurable hip joint prosthesis A, wherein a single receiving cavity (or tapered recess 50) adapted to interface with a further element having a correspondingly dimensioned tapered shank (here, shank 60) is present in the femoral stem 10, and that the femoral implant 1 has only one such juncture, which distinguishes over certain prosthetic implants known to the prior art; no additional intermediate body or element between the part of the prosthetic implanted in the femur and the part which contacts an acetabular cup or liner thereof is required as is characteristic of certain of said prior art prosthetics. Preferably also the central axial geometry of the single receiving cavity and the central axial geometry of the tapered shank are complementary, and at perpendicular cross-sections define a circle, such that the axial geometry of each is uniform of rotated about the central axis. Such may be a frustoconical section. Such distinguishes over irregular geometries, such as ellipsoids, and other shapes which have irregular perpendicular cross-sections along with their central axial geometry. Having a single juncture, and on in which the female part, viz, the single receiving cavity (or tapered recess 50) is present within the implanted femoral stem 10 ensures that the load imparted by the trunk and upper extremities of the human body is directed downwardly, providing an inherent compression in a direction towards the knee and foot, which ensures that the complementary shaped tapered shank (here, shank 60), which has a wider dimension at its proximal base part 62 than at a distal end thereof 61.

FIG. 4A and its cross-sectional view of FIG. 4B illustrates in a side view a femoral implant 1 which includes both a femoral stem 10 which with a slight tapers extends outwardly from a distal end 12 to a proximal and/or proximal region 14 containing a tapered recess 50 which is adapted to receive and retain a within which is removably seatable femoral ball 30 having a complementary tapered shank 60 which extends outwardly from a base part 32 thereof. While not shown in FIG. 4A, is to be understood that the femoral ball 30 can be substituted by a femoral cup which includes a similar complementary tapered shank 60

FIGS. 5A and 5C, and in FIG. 5A's cross-sectional view presented in FIG. 5B illustrates in a side view a femoral implant 1 which includes both a femoral stem 10 which with a slight tapers extends outwardly from a distal end 12 to a proximal and/or proximal region 14 containing a tapered recess 50 which is adapted to receive and retain a within a removably seatable femoral ball 30 having a complementary tapered shank 60 which extends outwardly from a base part 32 thereof. While not shown in FIG. 5A, is to be understood that the femoral ball 30 can be substituted by a femoral cup which includes a similar complementary tapered shank 60, FIG. 5C helpfully illustrates the femoral ball 30 separated from the femoral stem 10 and illustrates that these elements are separable from each other. FIGS. 5A and 5B illustrate an embodiment of a reconfigurable hip joint prosthesis A and elements used to configure the same. Further nonlimiting examples of femoral implants 1 and component parts thereof are illustrated in further drawing figures forming part of this patent application including those depicted on FIGS. 21E1 through 21E4, or FIGS. 22F1 through 22F63.

Figure 6C:
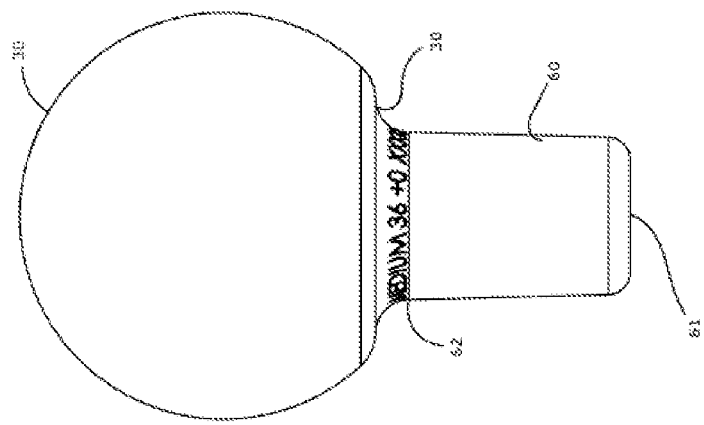
Figure 6B:
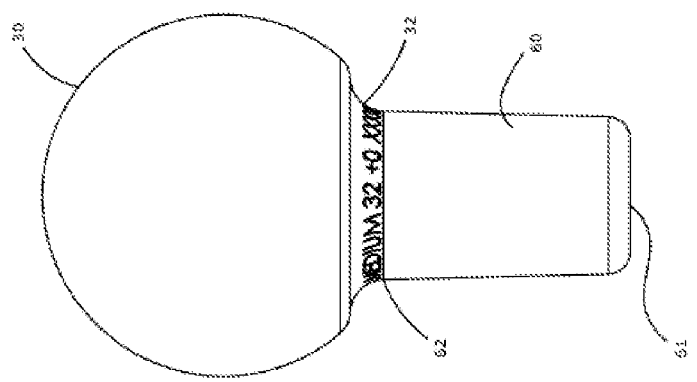
Figure 6A:
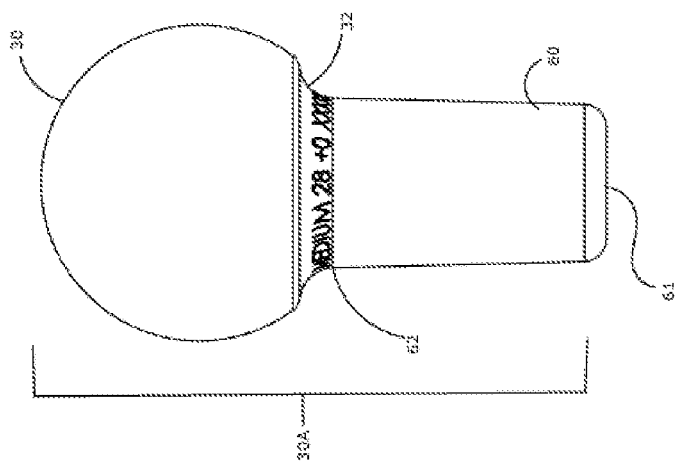

FIGS. 6A, 6B and 6C in a side view depict three embodiments of a femoral ball element 30A having femoral balls 30 having different sizes and configurations. Notably, be seen that the parts of each of the femoral balls 30 are substantially hemispherical, and include bases 32 from which depend shanks 60. The illustrated shanks normal 60 have varying lengths and various average diameters, and are Morse tapers. It is to be understood the configuration of the shank 60 necessarily include parts thereof which have complementary dimensions which are suitable for insertion into common retention within a recess 50. Further nonlimiting examples of femoral balls are illustrated in further drawing figures forming part of this patent application. These include those of FIGS. 17A1 through FIG. 17A9. Each of FIGS. 17A1-17A9 depict in elevational view various embodiments of femoral ball elements of different dimensions and configurations; with FIG. A4 providing a perspective view of an embodiment of a femoral ball element.

FIGS. 7A, 7B, 7C and 7D depict an alternative configuration of a femoral implant 1 comprising a femoral stem 10 element and affixable femoral ball element 30A. FIG. 7B is a cross section of FIG. 7A illustrates the femoral stem 10 separated from the component which comprises the femoral ball element 30A itself having a femoral ball 30 and base 32 which comprises a tapered recess 50 within, which is suitably dimensioned to be mounted upon a tapered shank 50' formed as part of the femoral stem 10 and extending outwardly from the proximal region 14 thereof. The degree of taper of the tapered recess 50 and/or of the tapered shank 50' extending from the proximal end 14 of the femoral stem may be as previously described, namely advantageously has an angle of between about 0.5 and 5 degrees of arc, preferably between about 1 and 3 degrees. Conventional configurations of such tapers are preferred, include one or more of: a Morse taper, a Jacobs taper, a Brown & Sharpe taper, a Jarno taper, with a Morse taper, especially Morse tapers having an angle of between about 1 and 3 degrees of arc. FIGS. 7C and 7D illustrate the component parts of this alternative configuration of the femoral implant 1 in an assembled form, where FIG. 7D is the cross-sectional view of FIG. 7C. FIGS. 7C and 7D illustrate an embodiment of a reconfigurable hip joint prosthesis A and elements used to configure the same. Further seen on FIGS. 7A, 7C are surface profiling on the exterior of the femoral stem 10 which may assist in the engagement of parts of femoral stem when inserted into a femur. Such surface profiling on the exterior the femoral stem 10 is advantageously used in revision surgery wherein it is necessary to replace a femoral insert, e.g. sometimes referred to as "revision surgery"; in such a revision surgery is contemplated that a prior art femoral implant or prior art femoral stem is replaced with a femoral implant or femoral stem as described herein with reference to the present invention. The surface profiling "P" may be any non-smooth surface or non-smooth surface feature, or element, which may advantageously improve the likelihood of retention within the femur when implanted. The way of nonlimiting example, such may be a non-smooth, roughened or textured surface, or may be comprise one or more outstanding elements such as the series of flutes or ribs P as depicted in the figures. Of course, the configurations, geometries, may also be used in place of the depicted flutes P. Also shown on FIGS. 7A-7D are one or more through holes "h" which, may be used to encompass a part of a retention element (not shown), such as surgical wire, suture, or other article or element passing therethrough which, for example may also be affixed to a part of the femur or other body structure, viz., bone, or other implanted element.

Femoral cups elements which are removably seatable within a femoral stem 10 or part thereof, particularly as described with reference to one or more of FIGS. 1A, 1B, 2A, 2B, 3A, 3B, 4A, 4B, 5A, 5B, and 7A, may be used with the femoral stem 10. A non-limiting example of a femoral cup element 40A is generally illustrated in the side cross-sectional view of FIG. 8 which depicts in detail a cross-sectional view of an implanted hip joint prosthesis of the present invention. Implanted into a femur F is a femoral implant 1 which is partially visible on the drawing, which comprises a shaft 10 and a pelvis P. A partial, cross-sectional view of a femoral implant 1 is illustrated in FIG. 8 a part of femoral implant 1 is only shown, but such includes a femoral stem 10 having a proximal and/or proximal region 14 containing a tapered recess 50 which is adapted to receive and retain a within a shank 60 which extends from a femoral cup 40, the shank 60 and femoral cup 40 being parts of the femoral cup element 40A. While not illustrated in this particular figure, the femoral cup 40 may include a lining as described with reference to acetabular cups described elsewhere herein. The femoral cup 40 has interfacial contact with an acetabular ball 78 which is mounted via ball recess 76, here a (preferred) tapered recess which is removably fitted upon a protrusion or stem 77 extending into the concave interior 79 the acetabular cup 70. It is to be understood that the acetabular ball 78 may be removed from the acetabular cup 70 by withdrawing it from the stem 77. The acetabular cup 70 is mounted to the pelvis P via conventional bone screws 90 extending through holes 74 and is thereby anchored thereto. It is to be understood however that the acetabular cup 70 and acetabular ball 78 may be removed if necessary, according to conventional surgical techniques if it is desired or necessary to replace the acetabular cup 70 of the invention with one of the same configuration as depicted in FIG. 8, or according to an alternative configuration.

Further depictions of femoral cups elements 40A are depicted in FIGS. 9A, 9B, 9C and 9D, with an alternative configuration of femoral cup elements 40A are depicted on FIGS. 10A, 10B, 10C and 10D. Both are within the ambit of the invention being taught herein.

Figure 9A:
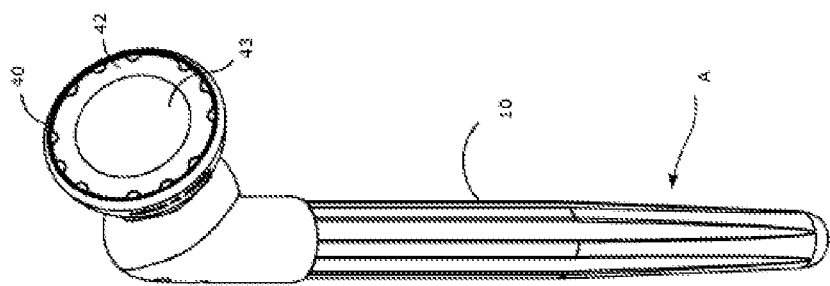
FIGS. 9A, 9B, 9C and 9D depict in various views and element configurations a femoral stem and a first embodiment of an affixable femoral cup element.
Figure 9B:
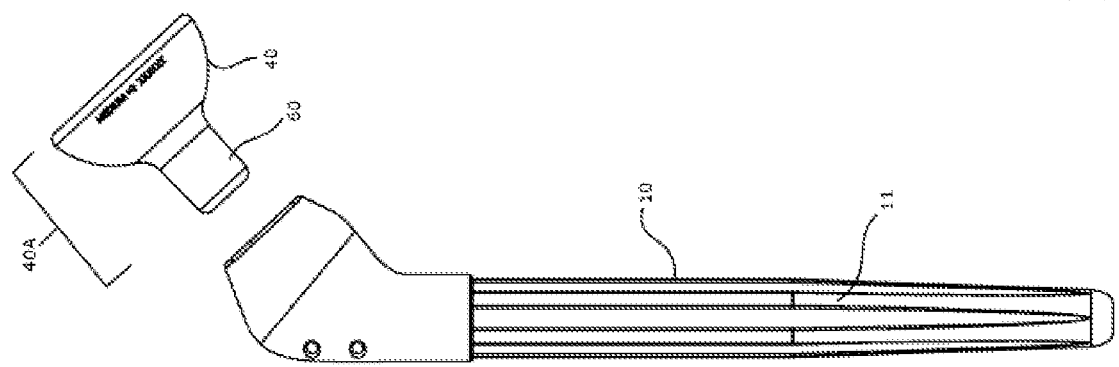
Figure 9C:
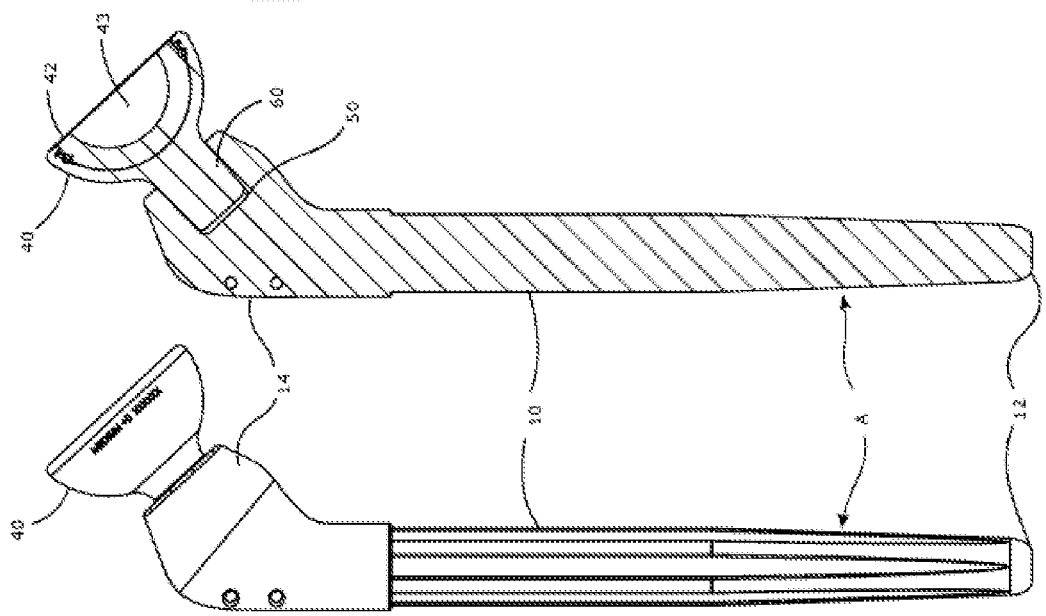
Figure 9D:

A femoral implant 1 is depicted in the side view in FIG. 9A which illustrates the femoral cup element 40A removably mounted upon a part of the femoral stem 10, and more particularly at a proximal end 14 thereof. FIG. 9B illustrates a side, cross-section of the femoral implant 1 of FIG. 9A, illustrating in further detail the femoral implant 40 and its shank 60 inserted into a correspondingly configured recess 50 within the proximal end 14 of the femoral stem 10. Further visible the figure is a femoral cup liner 42 inserted within the femoral cup 40, and having a liner recess 43 therein. The liner 42 may be formed of any material, such as ceramic, metal, metal alloy, but preferably is of a synthetic polymer (or copolymer) such as a polyolefin (preferably a highly crosslinked polyolefin, such as a highly crosslinked polyethylene) which provides lubricity to ensure smooth rotation and/or translation with a correspondingly configured acetabular ball (not shown in the figure). It is to be understood that the material of the femoral cup liner 42 may be of the same type used to form an acetabular cup liner 72 discussed previously, and in some cases may have configurations or features of one or more of the acetabular cup liners 72 discussed previously and depicted on further of the drawing figures included in this patent application. Such also applies, mutatis mutandis, FIG. 9C illustrates essentially the same view is that FIG. 9A, but illustrates the acetabular cup 40 separated from the proximal end of the femoral stem 10. FIG. 9D illustrates a perspective, frontal view of the femoral implant 1 of FIG. 9A and provides a more detailed view of the interior of the acetabular cup 40 and the liner 42. It is to be observed here that the configuration of the femoral stem 10 corresponds closely to the femoral stem 10 according to FIG. 4A, and such illustrates the principle that the femoral ball 30 as shown in FIGS. 5A, 5B and 5C are interchangeable with the femoral cup 40 illustrated on FIGS. 9A, 9B. Such a reconfiguration may occur in vivo within a patient's body, or external to a patient's body, e.g, prior to implantation within a patient's body. Also, such a reconfiguration does not require that the femoral stem 10 be removed from the femur.

Figures 10A, 10B, 10C, 10D:
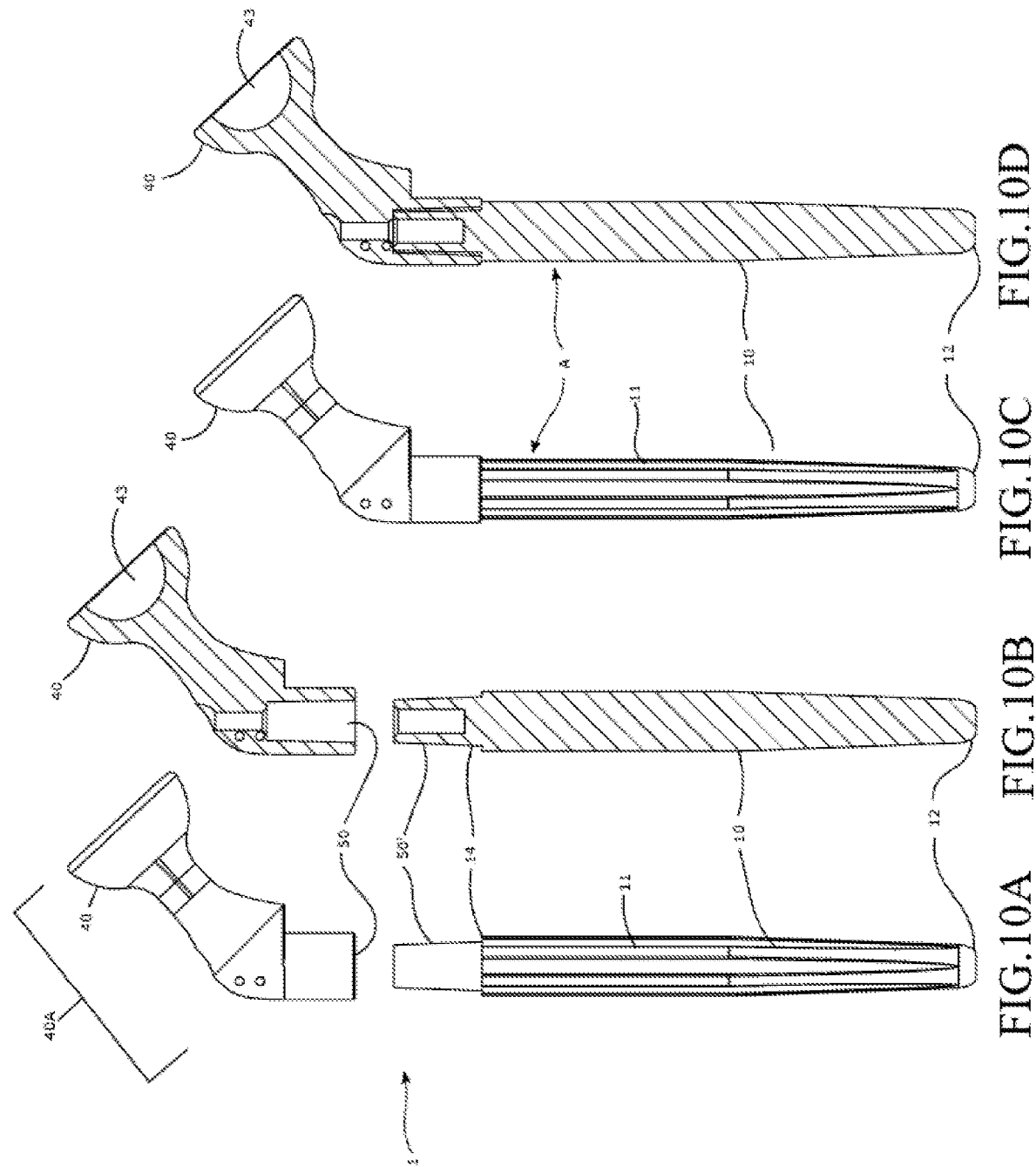
FIGS. 10A, 10B, 10C and 10D depict in various views and element configurations an alternate embodiment of a femoral stem and a different embodiment of an affixable femoral cup element.

Further femoral cup elements 40A are depicted on FIGS. 10A, 10B, 10C and 10D which depict a further embodiment of the femoral implant 1 according to the invention. FIG. 10A depicts a side view, and FIG. 10B illustrates a cross-section of FIG. 10A; in these views the femoral cup 40 is separated from the femoral stem 10. FIG. 10C illustrates a side view of the femoral implant of FIG. 10A however wherein the femoral cup 40 is mounted upon the femoral stem 10. FIG. 10D illustrates a cross-section of the view presented in FIG. 10C. It is to be noted here that the configuration of the femoral stem 10 corresponds closely to the femoral stem 10 according to FIG. 7A, and such illustrates the principle that the femoral ball 30 as shown in FIGS. 7A, 7B, 7C and 7D are interchangeable with the femoral cup 40 illustrated on FIGS. 10A, 10B, 10C and 10D. The femoral cup 40 of FIG. 10A includes tapered recess 50, which is suitably dimensioned to be mounted upon a tapered shank 50' formed as part of the femoral stem 10 and extending outwardly from the proximal region 14 thereof.

All types of acetabular cups may be utilized with certain embodiments of femoral implants according to invention, including those shown or described herein, as well as those not necessarily shown in any of the drawing figures; but it is to be expressly understood that any acetabular cup which are operable with a femoral ball or a femoral cup may be used and are considered to be within the scope of the present invention.

Acetabular cups which are useful when the femoral implant comprises a femoral cup include acetabular cups which contain an acetabular ball; reference is made to FIG. 8 which depicts a preferred embodiment thereof.

Acetabular cups which are useful when the femoral implant comprises a femoral ball include those conventionally known to the prior art. Essentially, these may be any acetabular cups which may be implanted in a pelvis, and which can receive a suitably dimensioned femoral ball. Nonlimiting examples of such types of acetabular cups 70 included those depicted on FIGS. 1C, 2C and 3C. Further examples of acetabular cups 7 include those depicted on FIGS. 11A, 11B, 11C, 11D, 12A, 12B, 13A and 13B.

FIGS. 11A, 11B, 11C and 11D, respectively, depict: a top plan view of the interior of, a side perspective view of the interior of, and elevation view, and a cross-section view of an embodiment of an acetabular cup 70. In the drawing figures, the acetabular cup 70 has a concave interior 79 which is curved or at least in part is hemispherical in configuration, as well as an exterior surface 71. The concave interior 79 is adapted to receive an acetabular cup liner 72 (not shown in the figure), after the acetabular cup 70 has been installed within a pelvis. The liner 72 may be press fit, snap fit, or retained by any suitable means including but not limited to a snap ring or elements near the edge 75 of the acetabular cup, by adhesive interposed between a part of the liner 72 and the acetabular cup 70, or any other means, or method known to the art. The acetabular cup 70 itself, as depicted in FIG. 11A may be mounted to a pelvis and retained their two by use of a bone cement, press fit, or any other means or method known to the art.

FIGS. 12A and 12B illustrate a top plan view and a side perspective view of a further embodiment of an acetabular cup 70, which is substantially similar to the acetabular cup according to FIG. 11A, but for including a plurality of through perforations 74. One or more of these through perforation 74 facilitates the use of bone screws, or other fasteners which may be inserted within and/or through one or more of the through perforations 74 and which is thereby mounted and retained to a pelvis.

FIGS. 13A, 13B illustrate a top plan view and a side perspective view of a further embodiment of an acetabular cup 70, which is substantially similar to the acetabular cup according to FIG. 11A, but for including a larger plurality of through perforations 74 then shown in FIGS. 12A and 12B, but differs in that no other significant manner. Again one or more of these through perforations 74 facilitate the use of bone screws, or other fasteners which may be inserted within and/or through one or more of the through perforation 74 and which is thereby mounted and retained to a pelvis.

With regard to acetabular cups, whereas the embodiment of FIGS. 11A, 11B, 11C and 11D depict an acetabular cup with no through holes, the embodiment of FIGS. 12A and 12B illustrate an acetabular cup with three through holes 74, and FIGS. 13A, 13B illustrate an acetabular cup with 12 through holes 74 it is to be understood that the number of, and the specific arrangement are positioning of the through holes 74 in an acetabular cup may vary widely. Further nonlimiting examples of acetabular cups are illustrated in further drawing figures forming part of this patent application. Such include those depicted on FIGS. 18B1 through FIG. 18B8, as well as on FIGS. 19C1 through FIG. 19C24. as well as in further drawing figures forming part of this application.

FIGS. 14A, 14B, 15A, 15B, 16A and 16B depict various embodiments an acetabular cup liner 72 which are adapted to be used in conjunction with one or more of the acetabular cups, particularly one or more of the acetabular cups 70 of FIGS. 11A, 11B, 11C, 11D, 12A, 12B, 13A and 13B.

FIG. 14A depicts a top plan view of an acetabular cup liner 72 and FIG. 14B illustrates a side perspective view thereof. The acetabular cup liner 72 insertable into and retainable within the concave interior 79 of an acetabular cup 70. The acetabular cup liner 72 comprises a recess 43 therein, which has a concave shape or profile adapted to come into interfacial contact with a femoral ball (not shown).

FIG. 15A depicts a top plan view of a further embodiment of an acetabular cup liner 72 and FIG. 15B illustrates a side perspective view thereof. The acetabular cup liner 72 is insertable into and retainable within the concave interior 79 of an acetabular cup 70. The liner 72 comprises a liner recess 43 therein, which has a concave shape or profile adapted to come into interfacial contact with a femoral ball (not shown). In particular, in this embodiment is seen that a portion 73 of the acetabular cup liner 72 is raised, such that when the acetabular cup liner 72 is installed acetabular cup 70, that portion 73 extends beyond the edge 75 of the acetabular cup 70, e.g, as shown in FIG. 2C. The raised portion 73 of the acetabular cup liner 72 forms an arcuate flat raised face 73' which is offset by an angle "a" from the arcuate flat face 72' of the acetabular cup liner 72; preferably angle "a" is between 0.5 and 35 degrees of arc, preferably is between about 5 and 25 degrees of arc. Thus, the arcuate flat raised face 73' ramps upwardly from the arcuate flat face 72' of the liner 72. Further preferably the raised portion 73 of the liner 72 encompasses at least about one-half (as illustrated by dotted line "1") of the circumference of the acetabular cup liner 72, as measured from the arcuate flat face 72' and the arcuate flat raised face 73'.

FIG. 16A depicts a top plan view of a still further embodiment of an acetabular cup liner 72 and FIG. 16B illustrates a side perspective view thereof. The acetabular cup liner 72 is insertable into and retainable within the concave interior 79 of an acetabular cup 70. The acetabular cup liner 72 comprises a liner recess 43 therein, which has a concave shape or profile adapted to come into interfacial contact with a femoral ball (not shown). In particular, in this embodiment is seen that portions 73 of the acetabular cup liner 72 is raised, such that when the acetabular cup liner 72 is installed acetabular cup 70, that the portions 73 extend beyond the edge 75 of the acetabular cup 70, e.g, as shown in FIG. 3C. Somewhat similar to the embodiment of FIGS. 15A, 15B, there is present a raised portion 73 of the acetabular cup liner 72 which includes both an arcuate flat raised face 73' which is offset by an angle "a" from the arcuate flat face 72' of the liner 72, and a second arcuate flat face 73" as well, which is parallel to but offset from the flat face 72'. Thus, the two faces 73' ramps upwardly from the arcuate flat face 72' of the acetabular cup liner 72, and extend to second arcuate flat face 73", Again, preferably angle "a" is between 0.5 and 35 degrees of arc, preferably is between about 5 and 25 degrees of arc. Further nonlimiting examples of liners are illustrated in further drawing figures forming part of this patent application. Such include those depicted on FIGS. D1 through D24, as well as in further drawing figures forming part of this patent application.

Certain preferred embodiments of the invention are disclosed on FIGS. 22F1-22F7 and 22F15 which depict in various views elements of a first embodiment of a reconfigurable hip joint prosthesis and elements therefor; FIGS. 22F3, 22F5 and 22F7 are respectively cross-sectional view of FIGS. 22F2, 22F4 and 22F6, and FIGS. 22F1, 22F6, 22F7 and 22F15 depict various views of an assembled a reconfigurable hip joint prosthesis A comprising and a femoral ball element 30A and a femoral stem element 10 having a fluted sidewall.

Certain alternative preferred embodiments of the invention are disclosed on FIGS. 22F8-22F14 and 22F16 which depict in various views elements of a further embodiment of a reconfigurable hip joint prosthesis and elements therefor; FIGS. 22F10, 22F12 and 22F14 are respectively cross-sectional view of FIGS. 22F9, 22F11 and 22F13, and FIGS. 22F8, 22F13, 22F14 and 22F16 depict an assembled a reconfigurable hip joint prosthesis A comprising a femoral cup element 40A and a femoral stem element 10 having a fluted sidewall in various views.

Certain further preferred embodiments of the invention are disclosed on FIGS. 22F17-22F24, 22F30 which depict in various views elements of another embodiment of a reconfigurable hip joint prosthesis and elements therefor; FIG. 22F19, 22F22 are respectively cross-sectional view of FIGS. 22F18 and 22F21, and FIGS. 22F21, 22F22 and 22F30 depict an assembled a reconfigurable hip joint prosthesis A comprising a femoral ball element 30A and a femoral stem element 10 having a fluted sidewall in various views.

Another preferred embodiment of the invention is disclosed on FIGS. 22F25-22F29 and 22F31 which depict in various views elements of another embodiment of a reconfigurable hip joint prosthesis and elements therefor; FIG. 22F27 is a cross-sectional view of FIG. 22F26, and FIGS. 22F26, 22F27 and 22F31 depict an assembled a reconfigurable hip joint prosthesis A comprising a femoral cup element 40A and a femoral stem element 10 having a fluted sidewall.

A yet further preferred embodiment of the invention is disclosed in FIGS. 22F32-22F38, and 22F47 which depict in various views elements of another embodiment of a reconfigurable hip joint prosthesis and elements therefor; FIGS. 22F35, 22F36 and 22F38 are respectively cross-sectional views of FIGS. 22F33, 22F34, and FIG. 22F37, and FIGS. 22F37, 22F38 and 22F47 depict an assembled a reconfigurable hip joint prosthesis A comprising a femoral ball element 30A and a femoral stem 10 having a smooth sidewall.

Another preferred embodiment of the invention is disclosed on FIGS. 22F42-22F46 and 22F48 which depict in various views elements of another embodiment of a reconfigurable hip joint prosthesis and elements therefor; FIGS. 22F43, 22F44 and 22F46 are cross-sectional views of FIGS. 22F41, 22F42 and 22F4, and FIGS. 22F45, 22F46 and 22F48 depict an assembled a reconfigurable hip joint prosthesis A comprising a femoral cup element 40A and a femoral stem 10 having smooth sidewalls.

A yet further preferred embodiment of the invention is disclosed in FIGS. 22F49-22F56 and 22F62 which depict in various views elements of another embodiment of a reconfigurable hip joint prosthesis and elements therefor; FIGS. 22F51 and 22F54 are respectively cross-sectional views of FIGS. 22F50 and 22F53, and FIGS. 22F52-22F54 and 22F62 depict in various views an assembled a reconfigurable hip joint prosthesis A comprising a femoral ball element 30A and a femoral stem 10 element having smooth sidewalls.

Another preferred embodiment of the invention is disclosed on FIGS. 22F57-22F61 and 22F63 which depict in various views elements of another embodiment of a reconfigurable hip joint prosthesis and elements therefor; FIG. 22F59 is a cross-sectional view of FIG. 22F59, and Figures 22F57, 22F58, 22F59 and 22F63 depict an assembled a reconfigurable hip joint prosthesis A comprising an femoral cup element 40A and a femoral stem 10 element having smooth sidewalls.

Any of the foregoing elements may be fabricated from suitable materials of constructions which are effective for their purpose, and preferably are also sterilizable and/or are biocompatible with surrounding tissue and bone. Nonlimiting examples which are useful to form parts of the femoral implant and part thereof include metals and metal alloys, particularly titanium and titanium alloys. Such metals are typically high strength, and are durable. With regard to non-metallic parts, synthetic polymers including those described with reference to liners of the invention are particularly preferred. However other materials such as ceramics may be used. Also any of the parts or components thereof may be provided with a coating material. Sucy may form a film. A number of coatings, such as in a composite or laminar layers may also be provided. Non-limiting examples of useful material for providing coatings include any materials which may be applied which impart a desired characteristic, e.g. improved adhesion such as with bone cement and/or inducement of bone growth. Non-limiting examples of coating materials include hydroxy acetate, calcium phosphates, as well as biological hydroxyl carbonated apatites formed on the surface of some implants, such as bioactive glasses, hydroxyapatite ceramics, as well as other bioactive materials, and the like. Also any of the parts or components thereof may be provided with non-smooth surface features, such as may be provided by mechanical or chemical etching, patterning, surface roughening, etc., which may also impart a desired characteristic, e.g. improved surface porosity, improved adhesion such as with bone cement or inducement of bone growth. Any of the foregoing elements may include at least one coating as well as non-smooth surface features.

With regard to the placement of a femoral stem, as disclosed herein, a femoral stem inserter (or other similarly operative apparatus or device) may be used for insertion of the femoral implant into part of the femur. Tools providing such a function are known to the art, and in fact be any tool which is effective in providing this function with the femoral stems described herein. In use, a femur is prepared to receive a part of the femoral stem, an upper part of the femoral stem is engaged by the a femoral stem inserted into the femur. After the proper placement of the femoral stem within the femur is confirmed, the femoral stem inserter withdrawn.

An acetabular cup impactor may be used for the placement of (or removal of) an acetabular cup to be implanted within the pelvis. Tools providing such a function are known to the art, and may in fact be any tool which is effective in providing this function. An acetabular cup impactor may be used to insert, and/or remove an acetabular cup from a pelvis. When suitably placed, the acetabular cup may be retained in a position, and the acetabular cup impactor may be removed. Subsequently, the acetabular cup may be affixed to bone, such as pelvic bone, by conventional means including but not limited to the use of one or more screws, fasteners, bone cement, or other materials or methods commonly used in hip replacement therapy. It is contemplated that other configurations and types of acetabular cup impactors and devices which provide an equivalent function may also be used according to one more aspects of the present invention.

As previously discussed the invention also includes a kit of component parts used in providing a configured implantable prosthesis as described herein. Such a kit may include a container, cartridge or tray having one or more elements of reconfigurable hip joint prosthesis. Contemplated are kits which include all necessary elements to provide a complete reconfigurable hip joint prosthesis. Also contemplated are kits which includes less than all elements necessary to provide a reconfigurable hip joint prosthesis.

In one aspect, a kit includes one or more femoral stems in conjunction with one or more, preferably a plurality of femoral balls. The provision of a plurality of (a) femoral balls having different configurations, i.e, different dimensions as depicted on FIGS. 1A-1C, and/or FIGS. 2A-2C, and/or FIGS. 3A-3C, and/or FIGS. 5A-5C, and/or FIGS. 6A-6C, FIGS. 7A-7D, and/or FIGS. 17A1-17A9, and/or FIGS. 22F1-22F7, and/or FIGS. 22F17-22F24, and/or FIGS.

22F32-22F38, and/or FIGS. 22F49-22F55 and/or FIGS. 22F64-22F72 provides an array of femoral balls which may be made available to a surgeon during a surgical procedure, and thus a suitably sized femoral ball is ready at hand for insertion into the patient. Such a kit may take the form of a tray or other container which provides the plurality of femoral balls in an ordered arrangement, i.e., in order of an increasing dimension.

In one aspect, a kit includes one or more femoral stems in conjunction with one or more femoral cups, preferably a plurality of femoral cups. The provision of a plurality of (b) femoral cups having different configurations, i.e., such depicted on FIGS. 9A-9D, and/or FIGS. 22F8-22F16, and/or FIGS. 22F25-22F31, and/or FIGS. 22F40-22F48, and/or FIGS. 22F57-22F63 provides an array of femoral cups which may be made available to a surgeon during a surgical procedure, and thus a suitably sized femoral cup is ready at hand for insertion into the patient. Such a kit may take the form of a tray or other container which provides the plurality of femoral cups in an ordered arrangement, i.e., in order of an increasing dimension.

In a further aspect is provided a kit which excludes the femoral stem component, but includes a plurality of (c) acetabular balls having different configurations. The provision of a plurality of (c) acetabular balls (i.e., acetabular ball 78, of FIG. 8) having different dimensions provides an array of acetabular balls which may be made available to a surgeon during a surgical procedure, and thus a suitably sized acetabular ball is available and at hand for insertion into the patient. Such a kit may take the form of a tray or other container which provides the plurality of acetabular balls in an ordered arrangement, i.e., in order of an increasing dimension.

In a further aspect is provided a kit which excludes the femoral stem component but includes a plurality of (a) femoral balls having different configurations. Such a kit may take the form of a tray or other container which provides the plurality of femoral balls in an ordered arrangement, i.e., in order of an increasing dimension.

In a further aspect is provided a kit excludes the femoral stem component but includes a plurality of (b) femoral cups having different configurations. Such a kit may take the form of a tray or other container which provides the plurality of femoral cups in an ordered arrangement, i.e., in order of an increasing dimension.

In a further aspect is provided a kit excludes the femoral stem component but includes a plurality of (c) acetabular balls having different configurations. Such a kit may take the form of a tray or other container which provides the plurality of acetabular ball in an ordered arrangement, i.e., in order of an increasing dimension.

In a yet further aspect a kit includes one or more trays, each tray comprising at least one element of a reconfigurable hip joint prosthesis wherein each tray is sealed against contamination to ensure that its contents are sterile prior to being opened, whereafter one or more elements may be removed and optionally returned to the tray.

In a still further aspect a kit includes one or more tools, guides, or ancillary devices, or apparatus which is useful in implanting, removal, or modification of one or more parts of the reconfigurable hip joint prosthesis.

In a yet further aspect a tray may include one or more tools, guides, or ancillary devices, or apparatus which is useful in implanting, removal, or modification of one or more parts of the reconfigurable hip joint prosthesis concurrently with one or more acetabular cups.

In a yet further aspect a tray may include one or more tools, guides, or ancillary devices, or apparatus which is useful in implanting, removal, or modification of one or more parts of the reconfigurable hip joint prosthesis concurrently with one or more femoral stems.

In a yet further aspect a tray may include one or more tools, guides, or ancillary devices, or apparatus which is useful in implanting, removal, or modification of one or more parts of the reconfigurable hip joint prosthesis concurrently with one or more (a) femoral balls.

In a yet further aspect a tray may include one or more tools, guides, or ancillary devices, or apparatus which is useful in implanting, removal, or modification of one or more parts of the reconfigurable hip joint prosthesis concurrently with one or more (b) femoral cups.

In a yet further aspect a tray may include one or more tools, guides, or ancillary devices, or apparatus which is useful in implanting, removal, or modification of one or more parts of the reconfigurable hip joint prosthesis concurrently with one or more (c) acetabular balls.

One or more trays may be containers such as sealable, optionally resealable, containers.

A kit may include one or more trays and/or containers as described above, with different trays (and/or containers) having different contents. The trays and/or containers may be of a single use variety, which are intended to be disposed following being opened for the removal of part of or all of its contents. Alternately the trays and/or containers may be of reusable variety wherein the tray and remaining contents are returned to a supplier, vendor or repackager for refilling of elements now missing from the tray and/or container and/or kit and refurbishment for subsequent use.

The invention also includes surgical methods for providing a reconfigurable hip joint prosthesis to a patient, preferably a human patient.

A first method includes the step of: providing component elements of a reconfigurable hip joint prosthesis as described herein to a surgeon or other medical professional during a surgical procedure; the component elements may be any one or more parts or elements of a reconfigurable hip joint prosthesis as disclosed herein but all parts of a complete reconfigurable hip joint prosthesis need not be provided or be available to the surgeon. Such a method may be used wherein an existing reconfigurable hip joint prosthesis previously implanted within a patient is reconfigured by replacement or removal of parts thereof, i.e., converting between a first configuration and a second configuration, or vice-versa, or alternately to replace one or more elements of an existing reconfigurable hip joint prosthesis without fully converting between a first configuration and a second configuration, or vice-versa.

In a preferred method, the method includes the step of: providing sufficient component elements of a reconfigurable hip joint prosthesis as described herein to a surgeon during a surgical procedure, such that the surgeon may assemble a complete reconfigurable hip joint prosthesis during the surgical procedure such that the complete reconfigurable hip joint prosthesis is implanted into the patient during the surgical procedure. the component elements may be any one or more parts or elements of a reconfigurable hip joint prosthesis as disclosed herein.

In this specification while the preferred embodiments disclosed have been discussed and disclosed with reference to an implantable hip joint prosthesis, and reference has been made to a femur, femoral stem, pelvis and acetabular cup, it is to be understood that the prosthesis and elements described herein may also find use a shoulder prosthesis, and may include a humeral implant implantable in a humerus, and a glenoidal cup implantable in the glenoid fossa. In such an embodiment which is useful in providing a shoulder joint prosthesis, the humeral implant may be configured to include either a ball (or similarly configured three-dimensional geometric surface) extending therefrom or alternatively, a humeral cup having a cavity or a socket, while the glenoidal cup may be is configured to have either a complementary cavity or a socket or a ball (or similarly configured three-dimensional geometric surface) at least partially within the glenoidal cup. In either configuration the humeral implant may be reconfigured to include a humeral cup or a ball (or similarly configured three-dimensional geometric surface) extending therefrom.

The invention claimed is:

1. A reconfigurable hip joint prosthesis adapted to be surgically implantable in a human body, having a femoral insert part of the prosthesis implantable in the upper femur and further having an integrated tapered recess at a proximal end thereof which is configured to interchangeably receive and to have affixed thereto:
  a femoral ball element having a ball part and an integrated tapered shank which is configured to be received into the tapered recess; or,
  a femoral cup element having a cup part and an integrated tapered shank which is configured to be received within the tapered recess, and wherein the cup part is configured to come into interfacial contact with an acetabular ball fitted upon a stem within a concave interior of an acetabular cup;
  wherein the femoral insert part may receive and be affixed to either the femoral ball element or the femoral cup element to form the reconfigurable hip joint prosthesis.

2. A reconfigurable hip joint prosthesis adapted to be surgically implanted in a human body, having a femoral insert part of the prosthesis implantable in the upper femur and further having a tapered shank at a proximal end thereof which is configured to interchangeably receive and to have affixed thereon:
  a femoral ball element having a ball part and an integrated tapered recess which is configured to receive the tapered shank; or,
  a femoral cup element having a cup part and an integrated tapered recess which is configured to receive the tapered shank, and wherein the cup part is configured to come into interfacial contact with an acetabular ball fitted upon a stem within a concave interior of an acetabular cup;
  wherein the tapered shank may receive and to be affixed to either the femoral ball element or the femoral cup element to form the reconfigurable hip joint prosthesis.

3. A kit of component parts adapted to provide a reconfigurable implantable hip joint prosthesis according to claim 1.

4. A kit of component parts adapted to provide a reconfigurable implantable hip joint prosthesis according to claim 2.

5. The kit of claim 3, wherein the kit comprises a femoral insert, at least two of the femoral ball elements having differently dimensioned balls and/or at least two femoral cup elements of differently dimensioned cups.

6. The kit of claim 4, wherein the kit comprises a femoral insert, at least two of the femoral ball elements having differently dimensioned balls and/or at least two femoral cup elements of differently dimensioned cups.

7. A method of surgically implanting into a human body the reconfigurable hip joint prosthesis according to claim 1.

8. The method of claim 7, wherein the reconfigurable hip joint prosthesis comprises a femoral insert, and wherein according to the method the femoral insert may be reconfigured, in vivo, without requiring the femoral insert to be withdrawn from the femur.

9. A method of surgically implanting into a human body reconfigurable hip joint prosthesis according to claim 2.

10. The method of claim 9, wherein the reconfigurable hip joint prosthesis comprises a femoral insert, and wherein according to the method the femoral insert may be reconfigured, in vivo, without requiring the femoral insert to be withdrawn from the femur.

* * * * *